(12) United States Patent
Wilson et al.

(10) Patent No.: US 8,751,017 B2
(45) Date of Patent: Jun. 10, 2014

(54) REINFORCED, COMPLIANT ELECTRODE ASSEMBLY

(71) Applicant: Neurostream Technologies General Partnership, Quebec (CA)

(72) Inventors: Willard Wilson, Minneapolis, MN (US); Thomas E. Cross, Jr., Minneapolis, MN (US)

(73) Assignee: Neurostream Technologies G.P. (CA)

( * ) Notice: Subject to any disclaimer, the term of this patent is extended or adjusted under 35 U.S.C. 154(b) by 0 days.

(21) Appl. No.: 13/682,351

(22) Filed: Nov. 20, 2012

(65) Prior Publication Data

US 2013/0150940 A1 Jun. 13, 2013

Related U.S. Application Data

(60) Provisional application No. 61/569,563, filed on Dec. 12, 2011.

(51) Int. Cl.
*A61N 1/00* (2006.01)
(52) U.S. Cl.
USPC .......................................................... 607/118
(58) Field of Classification Search
USPC ............................. 607/118, 44, 42; 174/126.1
See application file for complete search history.

(56) References Cited

U.S. PATENT DOCUMENTS

| | | | |
|---|---|---|---|
| 6,600,956 B2 | 7/2003 | Maschino et al. | |
| 2008/0004673 A1* | 1/2008 | Rossing et al. | 607/44 |
| 2008/0103407 A1 | 5/2008 | Bolea et al. | |
| 2010/0312320 A1* | 12/2010 | Faltys et al. | 607/118 |
| 2011/0147046 A1* | 6/2011 | Bonde et al. | 174/126.1 |
| 2011/0196445 A1* | 8/2011 | Bolea et al. | 607/42 |

OTHER PUBLICATIONS

PCT/US2012/066040 International Search Report and Written Opinion (10 pages).

* cited by examiner

*Primary Examiner* — Robert N Wieland
(74) *Attorney, Agent, or Firm* — Polsinelli PC

(57) ABSTRACT

An electrode assembly is described, which allows close and robust contact with a biological structure such as a nerve while simultaneously preventing compressive injury to the biological structure. The electrode assembly includes a compliant cuff body and at least one reinforcing element in an aspect. The reinforced compliant cuff body may expand and contract to accommodate swelling of underlying biological structures, to accommodate movements of the biological structures associated with body movements, and to closely fit biological structures with irregular or non-uniform cross-sectional profiles. The electrode assembly further includes at least one electrode for sending and/or receiving electric impulse data to/from the biological structure such as a nerve.

42 Claims, 24 Drawing Sheets

REINFORCED, COMPLIANT ELECTRODE ASSEMBLY

REFERENCE TO RELATED APPLICATIONS

This application claims priority to U.S. Provisional Patent Application No. 61/569,563 filed on Dec. 12, 2011, and entitled "A REINFORCED, COMPLIANT NERVE CUFF ASSEMBLY", which is hereby incorporated herein by reference in its entirety.

FIELD OF THE INVENTION

The present disclosure relates to electrode assemblies for stimulating and/or recording electrical impulses in a biological structure such as a nerve, and more particularly to an improved reinforced compliant cuff body design that increases the safety and performance of implanted cuff assemblies. The invention offers enhancements for accessing biological structures such as peripheral nerves, cranial nerves, spinal roots, and the like and is of particular advantage for small diameter nerves, nerves that change diameter due to swelling or growth, and/or nerves that change shape, diameter, and position due to body movement.

BACKGROUND

Electrode assemblies are used to record and stimulate nerve activity in the treatment of such nerve-related disorders as epilepsy, sleep apnea, and pain. These electrode assemblies typically include a structural body bearing one or more electrodes and one or more lead wires. The electrodes are typically maintained in contact with a nerve of interest, and connected by the lead wires to an external electrical device such as a control unit capable of processing neural signals and/or generating stimulus pulses to implement the treatment of the nerve-related disorder.

The design of the electrode assembly is critical for a safe and effective interface with the nerve. To optimally transmit electrical signals to and from the nerve in an efficient and noise-free manner, the electrode assembly may be designed to maintain the electrodes near the nerve of interest, typically using some sort of closed cuff situated around a longitudinal segment of the nerve, as illustrated in FIG. 1A in side view and in FIG. 1B in end view. Existing closed cuff electrode assemblies typically include a sheet or tube of deformable, non-conductive material that is wrapped and/or sealed around a longitudinal segment of a nerve; the closed nerve cuff body acts as a framework for holding the electrodes in position relative to the nerve and to electrically isolate the enclosed nerve and electrodes from surrounding tissue. However, because the nerve is a living tissue, the electrode assembly may also be designed to minimize damage to the nerve as a result of the mechanical interaction of the cuff of the electrode assembly with the nerve during implantation and subsequent use. Existing closed-cuff electrode assembly designs are typically fitted to be about 50% larger than the enclosed nerve to provide a continuous layer of electrical insulation and tolerable proximity of the electrodes to the nerve, while simultaneously avoiding the compression of the nerve, which may produce long-term nerve damage.

The fitting of any electrode assembly to a nerve poses a significant challenge in part due to the dynamic nature of peripheral nerves in vivo. For example, nerves in the trunk, neck, or limbs normally accommodate body movement by elongating, expanding, contracting or moving within the surrounding tissues of the trunk, neck, or limb. Any electrode assembly that interferes with such accommodation to movement may expose the nerve to pressures in excess of a compression damage threshold. In addition, any nerve, including relatively immobile nerves, may exhibit an acute inflammatory response characterized by swelling which may substantially increase the diameter of the nerve after placement of an electrode assembly. During an acute inflammatory response, the internal pressure causing the nerve to swell may be opposed by reactive forces from a closed cuff electrode assembly, producing a net compressive force on the nerve as illustrated in FIG. 2. Thus, a risk for compressive nerve damage exists for all nerves, including stationary nerves, that are fitted with nerve cuff bodies that precisely match the nerve's original unperturbed diameter.

The mechanical interaction of an electrode assembly with a peripheral nerve is particularly important because peripheral nerves are known to be highly susceptible to mechanical insult. External pressure on a peripheral nerve may result in ischemia, edema, demyelination, axonal degeneration, impaired axonal transport, and/or the disruption of the nerve's conduction of impulses. The degree and extent of nerve damage is known to be related to the magnitude of compressive force induced by the electrode assembly, and long-term nerve damage may occur at pressures greater than about 20-30 mm Hg.

The most common approach to avoid compression injury is to use a purposely oversized nerve cuff assembly as described herein previously that provides an empty space for the nerve to swell into, as illustrated in FIG. 3A in side view and in FIG. 3B in end view. For example, the Association for the Advancement of Medical Instrumentation recommends that nerve cuff diameters exceed the diameter of the nerve by at least 50% to accommodate this acute inflammatory response. Although an oversized nerve cuff may effectively accommodate nerve swelling, any open space between the nerve and electrode may attenuate any electrical signals propagating to and/or from the nerve in this region. For recording applications, the oversized cuff may decrease the amplitude of the nerve signals that reach the sensing electrode. For stimulation applications, the oversized cuff may decrease the amplitude of stimulus pulses that reach the nerve. Oversized cuffs may also permit relative motion between the electrode assembly and the nerve, thereby randomly changing the location and separation distance of the open space between the nerve and the electrodes and introducing variability in the effective amplitude of recording and stimulation signals. The compromised electrical performance of oversized cuffs may be further diminished by in-growth of tissue or formation of a capsule in the empty space between the nerve and nerve cuff body, thereby further increasing the electrical impedance between the nerve and electrodes and further mitigating detection of neural signals and electrical transmission of stimulation pulses.

Other existing electrode assembly designs have attempted to address the issue of accommodating variation in size and movement of nerves. Existing helix electrode assemblies and split cuff electrode assemblies use an open design that does not completely encircle the nerve, but instead uses an open structure to accommodate nerve swelling and movement without compression. However, this open design functions poorly as an electrical insulator by allowing current to flow easily in and out of the openings in the open electrode assembly. This current flow through the openings causes attenuation of the signals to and/from the nerve and introduces noise to these signals due to entry of external signals. Existing spiral cuff electrode assembly designs include a cuff with a spiral cross section that accommodates nerve swelling without oversizing the assembly or exposing large sections of nerve. Although the spiral design provides a continuous layer of insulation without using a confining fixed closure mechanism, there exists significant risk of entrapment and/or compression of nerve tissue between the overlapping layers of the spiral cuff.

A need exists for a cuff body design for an electrode assembly that combines the mechanical safety advantages of a loosely-fitting or open cuff body design, as well as the efficient and low-noise electrical signal propagation performance of a closely-fitting closed cuff or spiral cuff design.

SUMMARY

The present disclosure relates to a reinforced, compliant electrode assembly, and methods of using and manufacturing the electrode assembly. The electrode assembly may be used to situate electrodes in close proximity to a variety of biological structures including, but not limited to, nerves. Although the electrode assembly is typically described herein below in the context of situating electrodes in close proximity to nerves, the electrode assembly may be used with a variety of other biological structures, as described herein below.

The invention safely accommodates changes in nerve size and shape by expanding and contracting along with the nerve while simultaneously maintaining a continuous and close-fitting layer of insulation that maintains the electrodes situated in close proximity to the nerve. The compliance of the electrode assembly, which includes electrodes attached to a cuff body, results from the combination of the cuff body's architecture and the properties of the materials used to construct the cuff body in various aspects. The reinforcement of the electrode assembly is designed to realize the safety and electrical benefits of a highly compliant closed cuff body while providing the mechanical strength necessary to manufacture and handle the electrode assembly and to maintain the electrodes in position relative to the nerve during use. In particular, the reinforcement protects the compliant cuff body from breaking, tearing, irreversible deformation due to stretching, and any other type of structural damage.

In one aspect, a reinforced compliant cuff body is provided that includes a compliant cuff body and one or more reinforcing elements attached to the compliant cuff body. The compliant cuff body is bounded by opposed and parallel first and second longitudinal edges, and further includes opposed inner and outer surfaces. The mechanical strength of the reinforced compliant cuff body is greater than the mechanical strength of the compliant cuff body alone.

In another aspect, a reinforced compliant cuff body is provided that includes a compliant reinforcing mesh and a compliant coating attached to the reinforcing mesh. The compliant reinforcing mesh is bounded by opposed parallel first and second longitudinal edges and includes a network of interconnected fibers defining a plurality of openings. The compliant coating, which forms the cuff body, surrounds each of the interconnected fibers and forms a film spanning each of the plurality of openings.

In an additional aspect, an electrode assembly is provided that includes a compliant cuff body, one or more reinforcing elements attached to the compliant cuff body, at least one electrode attached to an inner surface of the compliant cuff body, and at least one lead electrically connected to the at least one electrode at an attached end. The compliant cuff body is bounded by opposed parallel first and second longitudinal edges and also includes opposed inner and outer surfaces. The at least one lead includes an elongate conductive element and extends from the inner surface to the outer surface of the compliant cuff body. The mechanical strength of the electrode assembly is greater than the mechanical strength of the compliant cuff body.

In another additional aspect, a method of producing a reinforced cuff body is provided. The method includes contacting a reinforcing mesh with an uncured liquid elastic material. The reinforcing mesh includes a network of interconnected fibers defining a plurality of openings. Upon curing, the uncured liquid elastic material forms an elastic material coating over the reinforcing mesh and the plurality of openings.

Other features and iterations of the invention are described in more detail below.

BRIEF DESCRIPTION OF FIGURES

The figures illustrate various aspects of the embodiments.

FIG. 9C is a top view of the reinforced cuff body during extension.

FIG. 10C is a top view of the reinforced cuff body during extension.

FIG. 11C is a graph summarizing the load-deflection characteristics of the reinforced cuff.

FIG. 14C is an end view of the reinforced cuff body in a tubular configuration.

FIG. 19C is a top view of the cuff body in a stretched configuration.

FIG. 20C is a close-up end view of the coated deformable mesh material; FIG. 20D is a close-up top view of the deformable mesh material.

Corresponding reference characters and labels indicate corresponding elements among the views of the drawings. The headings used in the figures should not be interpreted to limit the scope of the claims.

DETAILED DESCRIPTION

Figure 1:
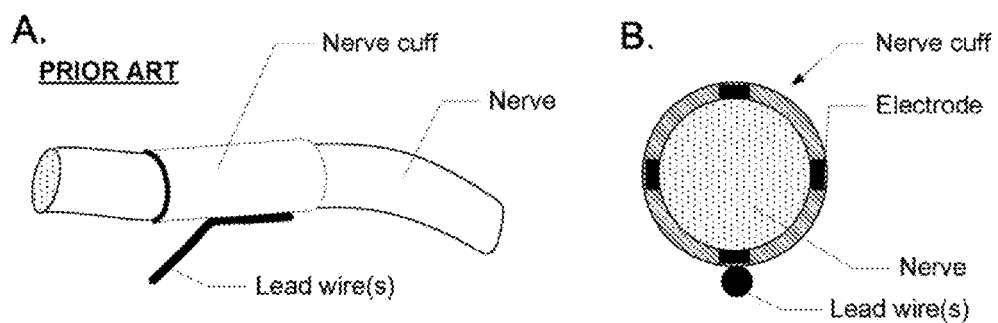
FIG. 1 is a side view (FIG. 1A) and an end view (FIG. 1B) of an existing closed cuff electrode assembly design.

The present disclosure describes reinforced, compliant, and close-fitting electrode assemblies with mechanical and electrical characteristics designed to safely and effectively access biological structures such as peripheral nerves. The disclosure also describes reinforced and compliant lead body assemblies of similar construction. Methods for manufacturing and using the electrode and lead body assemblies are also described in various disclosures.

I. Electrode Assembly

FIGS. 4A-4C are a top view (FIG. 4A), an end view (FIG. 4B), and a side view (FIG. 4C) of an electrode assembly 100 prior to placement on a nerve in an aspect. In this aspect, the electrode assembly 100 may include a cuff body 102 in the form of a sheet with an outer surface 106 and an opposed inner surface 104. The sheet forming the cuff body 102 may further be bounded by a first longitudinal edge 108, a second longitudinal edge 110, a first circumferential edge 112 and a second circumferential edge 113. The first and second longitudinal edges 108 and 110 are situated opposite to each other, and the first and second circumferential edges 112 and 113 are similarly situated opposite to each other to form the lateral boundaries of the cuff body 102. In an aspect, the cuff body 102 may be constructed with a compliant design in order to accommodate changes in the size and/or shape of the nerve to which the cuff body 102 is attached during use of the electrode assembly 100 and to return to its original shape when the deforming forces have been removed. For example, the cuff body 102 in this aspect may stretch to accommodate a swelling of an enclosed nerve, and may rebound to its original shape when the swelling of the enclosed nerve has subsided. A detailed description of the materials and construction of the cuff body 102 are provided herein below.

The electrode assembly 100 may further include a lead body 114 attached to the outer surface 106 at an attached body end 116 such that the opposite free body end 118 projects away from the outer surface 106. The lead body 114 may further include at least one electrical lead 120 embedded within the lead body 114. Depending on the particular design and/or intended use of the electrode assembly 100, each lead 120 may provide an electrical connection to carry electrical signals to and/or from the nerve to an external device such as an electrical control box (not shown). In various aspects, each lead 120 may be connected to the external device at one end, and at the lead's opposite end to either a ground electrode (not shown) situated on the outside of the cuff body 102 or to a recording or stimulating electrode 122 situated on the inside of the cuff body 102.

Figure 4:
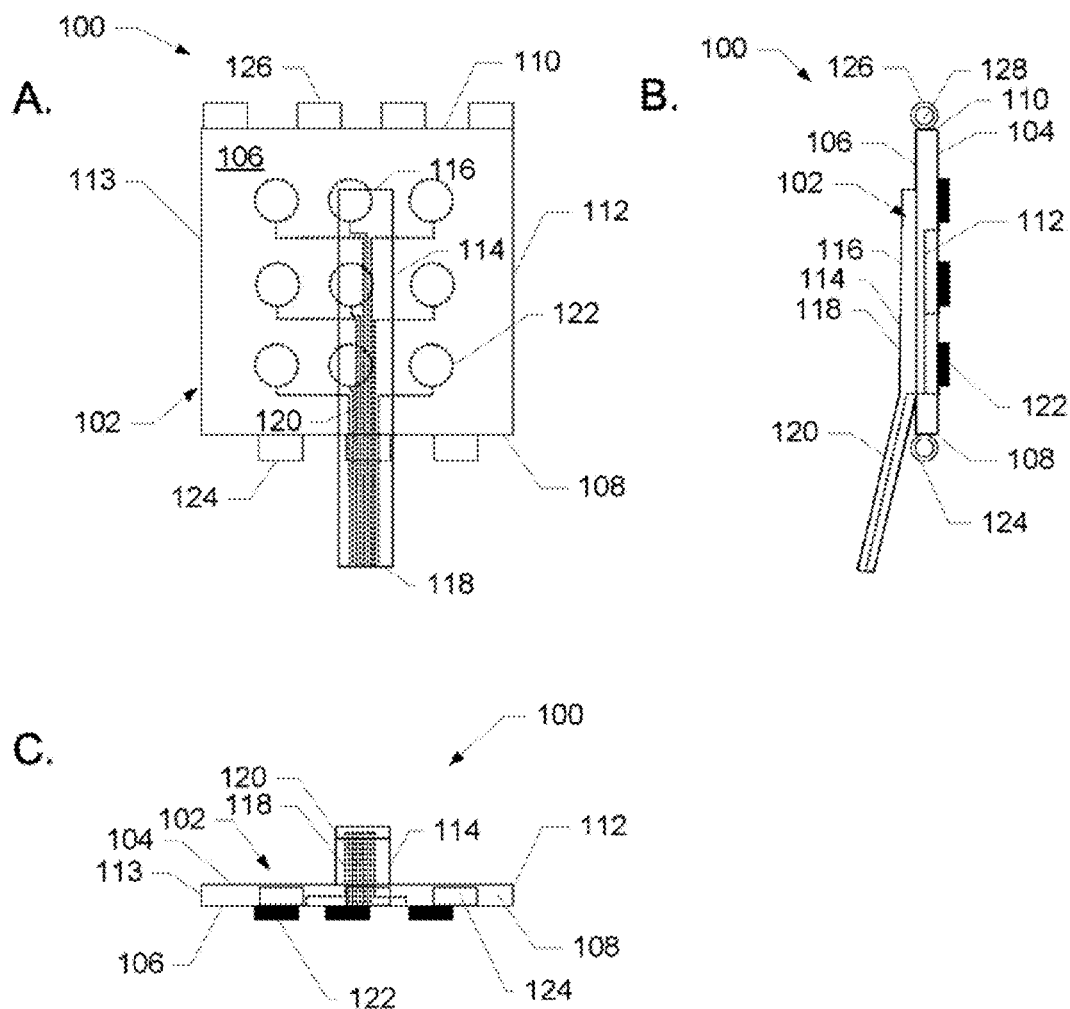
FIG. 4 is a top view (FIG. 4A), an end view (FIG. 4B), and a side view (FIG. 4C) of a cuff body.

The electrode assembly 100 may further include one or more first closure elements 124 attached to the first longitudinal edge 108 and one or more second closure elements 126 attached to the second longitudinal edge 110 of the cuff body 102. In general, the first and second closure elements 124 and 126 interact mechanically to reversibly join the first and second longitudinal edges 108 and 110 together during placement of the electrode assembly 100. In one aspect, the first and second closure elements 124 and 126 may be interdigitating tubular segments, as illustrated in FIG. 4. In this aspect, each of first and second closure elements 124 and 126 may define a lumen oriented in a direction parallel with the first and second longitudinal edges 108 and 110.

FIGS. 5A-5C are a top view (FIG. 5A), an end view (FIG. 5B), and a side view (FIG. 5C) of the electrode assembly 100 illustrated in FIG. 4 after placement on a nerve 202. The inner surface 104 of the cuff body 102 may be wrapped around the nerve 202 in order to situate the one or more electrodes 122 in contact with the nerve 202. The first and second longitudinal edges 108 and 110 may be joined and reversibly fastened by means of the mechanical interaction of the at least one first closure element 124 and the at least one second closure element 126. In this aspect, the first and second closure elements 124 and 126 may be interdigitated, and a deformable pin 204 may be inserted through the lumens 128 of each first and second closure elements in forward or reverse sequence: 126A, 124A, 126B, 124B, 126C, 124C, and 126D. In this closed configuration, the nerve 202 may protrude longitudinally from a first cuff opening 206 defined by the first circumferential edge 112 and a second cuff opening 208 defined by the second circumferential edge 113.

The electrode assembly 100 overcomes the limitations of existing electrode assembly designs by incorporating reinforcement that allows the use of thin layers of elastic materials in the construction of the cuff body 102 while imparting mechanical strength sufficient to avoid damage such as tearing of the cuff body 102. The elastic material's thin dimension and material properties synergistically combine to form a compliant cuff body 102 that may expand, contract and otherwise change shape along with the nerve 202 during use, while simultaneously maintaining continuous proximity and relative positioning between the nerve 202 and the at least one electrode 122. As a result, the electrode assembly 100 provides a means of efficiently obtaining electrical signals from the nerve 202 while attenuating the confounding effects of electrical noise arising from external electrical signals and/or leakage of current outside of the volume enclosed by the inner surface 104 of the cuff body 102.

A detailed description of various aspects of the electrode assembly 100, methods of producing the electrode assembly 100, and methods of using the electrode assembly 100 are provided herein below.

a. Properties of Electrode Assembly

In various aspects, the mechanical and electrical properties of the electrode assembly 100 are selected in order to implement the safe and accurate recording and delivery of electrical signals to and/or from an external device such as an electrical controller or an electronic data acquisition device. As described previously, a snug fit of the closed cuff body 102 of the electrode assembly 100 may enhance the efficiency of electrical signal transmission and reduce the introduction of noise from external sources. In various aspects, the electrode assembly 100 may be designed to be compatible with a wide variety of nerves.

The electrode assembly 100 may be used to transmit electrical signals to and/or from a nerve of any known size, type, or any other known nerve classification without limitation. Non-limiting examples of nerves compatible with the electrode assembly 100 include: a small diameter nerve, a curved nerve, and a mobile nerve. As used herein, a small diameter nerve refers to any nerve or portion of a nerve having a diameter ranging from about 0.5 mm to about 2 mm. As used herein, a curved nerve refers to any nerve or portion of a nerve that is non-linear in configuration when substantially in its normal, static in vivo position, though it may be exposed for the purpose of recording. A mobile nerve, as used herein, refers to any nerve or portion of a nerve that is free to move within the body. For example, mobile nerves may flex, stretch, bend, or move in conjunction with the motion of musculoskeletal system.

The electrode assembly 100 is compatible for use with nerves located in a vertebrate patient without limitation. Non-limiting examples of suitable vertebrate patients include fish, amphibians, reptiles, birds, and mammals. In an aspect, the electrode assembly 100 may be used to transmit signals to and/or from any peripheral nerve of a human patient situated outside of the brain and away from the spinal cord without limitation. Non-limiting examples of suitable peripheral nerves of a human patient include the internal branch of the superior laryngeal nerve, the external branch of the superior laryngeal nerve, the glossopharyngeal nerve, the phrenic nerve, the vagus nerve, the facial nerve, the trigeminal nerve, the hypoglossal nerve, the tibial nerve, and the common peroneal nerve.

In various aspects, the cuff body 102 of the electrode assembly 100 is wrapped snugly around a longitudinal segment of a nerve in order to situate the electrodes 122 in close proximity to the nerve. It is desirable for cuff body 102 to exhibit a number of compliant mechanical properties, so that the cuff body 102 may expand, contract and otherwise change shape with the nerve, while simultaneously maintaining continuous proximity between the nerve and the electrodes 122.

i. Mechanical Properties

In various aspects, the cuff body 102 is designed to be compliant in its axial, radial, and/or circumferential dimensions allowing for temporary swelling of the nerve following implantation and for changing size and shape of the nerve during body movement. The compliant nature of the cuff body 102 allows the electrode assembly 100 to accommodate changing nerve shape and to maintain close and constant physical proximity to the nerve while reducing shear forces and abrasion along the contact surface between the nerve and the cuff body 102. In an aspect, the compliant cuff body 102 is designed to be self-sizing and to return to its original starting diameter and shape after any nerve swelling has resolved or motion of the nerve has ceased. In this aspect, the cuff body 102 may be sufficiently compliant to maintain close contact along a curved nerve, and/or around a nerve that has an irregular cross section, such as an elliptical cross-section.

Figure 2:
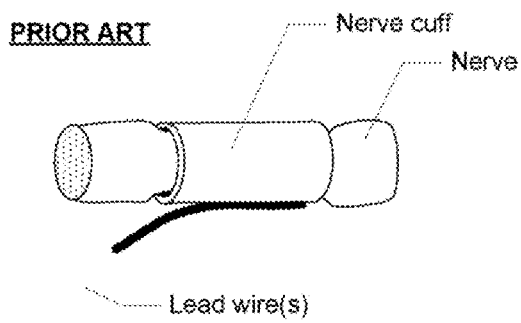
FIG. 2 is a side view of an existing closed cuff electrode assembly design in which a swollen nerve is compressed by the closed cuff.
Figure 3:
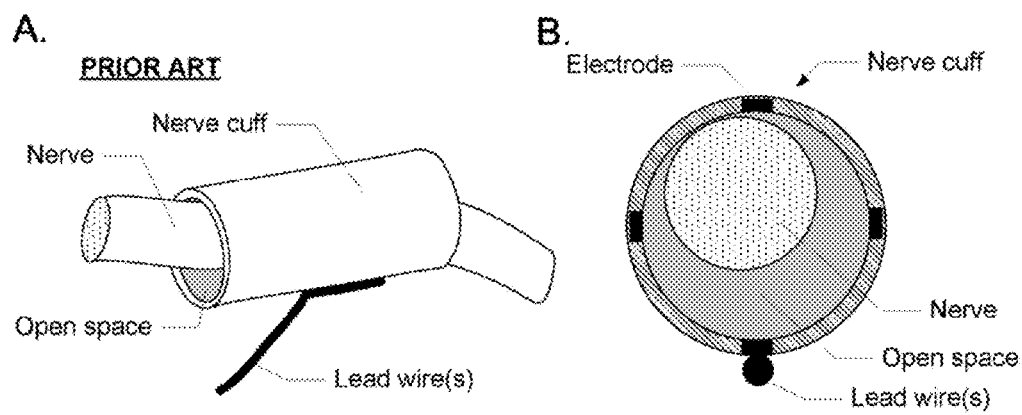
FIG. 3 is a side view (FIG. 3A) and an end view (FIG. 3B) of an existing closed cuff electrode assembly design in which the cuff is oversized relative to the nerve diameter.

The compliant, yet closely fitting cuff body 102 of the electrode assembly 100 ameliorates many issues associated with a cuff body 102 that is installed either too loosely or too tightly around a nerve. An oversized and loose-fitting cuff body 102 (see FIG. 3) may potentially damage the nerve by allowing the cuff body 102 to slide along the axial, radial, and/or circumferential dimensions of the nerve. This relative movement between the cuff body 102 and the underlying nerve may cause abrasions, reduced circulation, and/or compressive nerve injury, particularly near the edges of the cuff body 102. As discussed herein previously, a nerve may be compressed by a cuff body 102 that is too tight, creating compressive nerve damage (see FIG. 2). The cuff body 102 of the electrode assembly 100 may be configured to stretch and thereby accommodate swelling of the nerve to a diameter of up to 150% of the original nerve diameter without applying a pressure of more than 20 mm Hg to the underlying nerve. Without being limited to any particular theory, it is known in the art that nerve compression injury may occur if the pressure placed on a nerve exceeds about 20 mm Hg.

In various aspects, the compliant properties of the cuff body 102 result from the synergistic interaction of the material properties of the material of the cuff body 102 and the dimensions of the cuff body 102 such as the thickness of the material.

The elasticity of a material may be expressed in terms of Young's modulus E, which may be determined empirically using for example an Instron machine which quantifies the deflection of a sample of a material in response to a known force. Without being limited to any particular theory, an applied force may stretch a material sample in proportion to the applied force, the cross-sectional area of the sample being loaded by the force, and the Young's modulus E of the material. Materials with a linear relationship between applied force and deflection are said to undergo elastic deformation and typically return to their original shape after the applied force is removed. Materials that stretch a small distance when a given force is applied are considered to be less elastic and have a higher Young's modulus E than other materials which stretch more in response to the same given force; these more elastic materials are characterized by a lower Young's modulus E.

The dimensions of the cuff body 102, in combination with the properties of the cuff body material, may further influence the cuff body's overall compliance. Non-limiting examples of dimensions of the material that may influence the compliance of the cuff body 102 include: the thickness of the material; the width of the material, defined herein as the distance between the two circumferential edges 112 and 113; the diameter of the cuff body 102 situated around a nerve, and any combination thereof.

The thickness of the elastic material used to construct the cuff body 102 may influence the compliance of the cuff body 102 in one aspect. For example, a cuff body 102 that includes a very thick layer of material will resist stretching to a higher degree than a cuff body 102 that includes a thin layer of the same material. Even if the material of the cuff body 102 is relatively elastic, a thick cuff will be relatively non-compliant.

The diameter of the cuff body 102 may further influence its compliance. Because the cuff body 102 exerts reactive forces on the underlying nerve in the form of a pressure (i.e. a force divided by an area), the surface area of the nerve underlying the cuff body 102 influences the compliance of the cuff body 102 as well. For relatively small nerves (i.e. nerves with a small diameter), relatively modest compressive forces exerted by the cuff body 102 may translate to relatively large applied pressures on the underlying nerve.

The compliance of the cuff body 102 in an aspect will be influenced simultaneously by the elasticity of its material, the thickness of its material, as well as the radius of the underlying nerve. Without being limited to any particular theory, the compliance of the cuff body 102 fastened around a nerve that is undergoing swelling may be governed by the relationship of the elasticity of the material of the cuff body 102 as quantified by Young's modulus E, the thickness of the material in the cuff body 102 and the radius of the underlying nerve as expressed in Eqn. I:

$$\Delta r = \frac{r_c^3 \Delta P}{E[(r_c + h)^2 - r_c^2]} \left[ (1-v) + (1+v)\frac{(r_c + h)^2}{r_c^2} \right] \quad \text{Eqn. (I)}$$

where: $r_c$=original cuff/nerve radius; $\Delta P$=the change in internal pressure during swelling; E=Young's modulus for the cuff body material; h=cuff body wall thickness; v=Poisson's ratio for the cuff material; and $\Delta r$=the change in cuff radius. Poisson's ratio v, as used herein, refers to the transverse to axial strain ratio; v quantifies the degree to which the cross-section of a material will contract when stretched. A material that becomes relatively skinny when stretched would possess a relatively high v; many materials typically have a v of about 0.5.

Eqn. (I) describes the degree to which a nerve and surrounding cuff body 102 would change in size ($\Delta r$) due to a given change in internal nerve pressure ($\Delta P$). To estimate the amount of swelling that may be accommodated without compressive nerve injury, a pressure of 20 mm Hg, known in the art as a nerve damage threshold pressure, may be specified as $\Delta P$. By way of example, the mechanical properties of a commercially available silicone sheet material commonly used to form cuff bodies of existing devices (SILASTIC®; E=2.5 N/mm², h=300 μm, v=0.5) were substituted into Eqn. (I) along with an initial radius ($r_c$) ranging from 0 mm to about 7 mm. Using $\Delta P$=20 mm Hg, Eqn. (I) was solved for the change in size ($\Delta r$).

Figure 6:
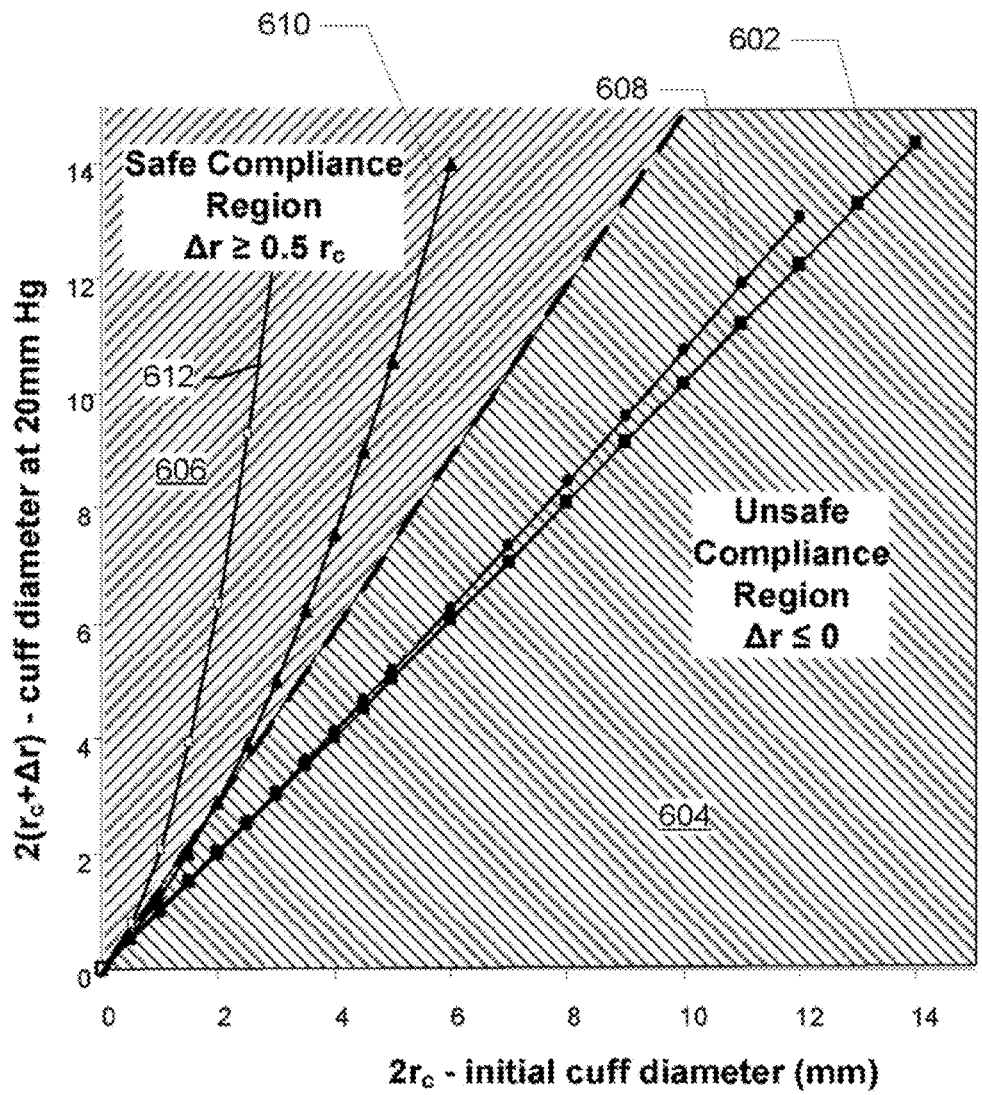
FIG. 6 is a graph summarizing the estimated compliance characteristics of several prototype cuff bodies.

The estimated compliance, quantified in this instance as the amount of swelling that may be safely accommodated by SILASTIC® cuff bodies for a range of initial nerve sizes as estimated by Eqn. (I), is summarized in FIG. 6 as line 602. Comparing line 602 to an unsafe compliance region 604, the SILASTIC® cuff may stretch only to a limited degree above initial cuff diameters larger than about 6 mm. A safe compliance region 606 is also illustrated in FIG. 6, corresponding to a cuff body which stretches to at least 150% of its initial diameter under a pressure of 20 mm Hg or less. Cuff bodies exhibiting a safe compliance falling within region 606 would be capable of accommodating a nerve swollen to as much as 150% of its initial diameter without imparting a pressure in excess of the 20 mm Hg damage threshold. As illustrated in FIG. 6, cuff bodies constructed from the SILASTIC® sheet material, summarized in line 602, fail to exhibit safe compliance at any cuff body diameter.

All else being equal, the compliance of a cuff body 102 may be enhanced by incorporating a more elastic material for cuff body construction in an aspect. For example, a cuff body material with an elasticity that approximately matches the corresponding elasticity typical of nerve tissue may be used for cuff body construction. Referring back to FIG. 6, the estimated amount of swelling that may be safely accommodated by a cuff body 102 constructed of a material with a Young's modulus of 0.6 N/mm² to match the Young's modulus of peripheral nerve tissue is summarized as line 608. Although the tissue-matched cuff body 102 of line 608, which had the same material thickness as the SILASTIC® cuff 602, results in a slight improvement in overall compliance characteristics, it still lies below the safe compliance region 606.

While elasticity does play a significant role in overall cuff body compliance, it should be pointed out that elasticity is solely a property of a material. It is the architecture of a structure containing the material, in combination with the characteristics of the materials such as elasticity, that give rise to the overall mechanical compliance of a structure. Compliance, as used generally herein, refers to the degree to which structures are deformed by an applied force and return to their original shape after the applied force is removed. Compliant structures are characterized by linear and reversible force/deflection relationships for a range of force magnitudes expected during use of the structure. A structure with high compliance, as used herein, refers to a structure such as a cuff body that readily stretches in response to an applied force and returns to its original shape after the applied force is removed. A structure with low compliance, as used herein, refers to a structure such as a cuff body that stretches a relatively small amount, if at all, in response to an applied force and returns to its original shape after the applied force is removed. A non-compliant structure, as used herein, refers to a structure such as a cuff body that does not stretch at all in response to an applied force for a range of force magnitudes expected during use of the structure.

For cuff bodies, the material thickness and the cuff radius are elements of the structure's architecture that contribute to a cuff body's overall mechanical compliance. When the tissue-matched material of line 608 with a material thickness of 10 μm is used to construct a cuff body rather than the 300 μm used previously, cuff bodies with safe compliance may be constructed for use with nerves having initial diameters as low as about 3 mm diameter, as illustrated by line 610.

However, without being limited to any particular theory, the cuff material thickness, the cuff radius and the Young's modulus of the cuff material may trade-off in counterintuitive ways. For example, cuff bodies made from highly elastic materials may be less compliant than cuff bodies made from less elastic materials but having thinner walls or larger diameters. As an extreme example, the compliance characteristics of a cuff body constructed from a hypothetical Hookean polymer with a Young's modulus matching that of diamond (E~1, 220,000 N/mm²) and a material thickness of about 1 picometer are summarized as line 612 in FIG. 6. A diamond-matched cuff body (line 612) in theory would exhibit safer compliance characteristics than thicker cuff bodies built from more elastic tissue-matched materials (lines 608 and 610) or from SILASTIC® (line 602).

Figure 7:
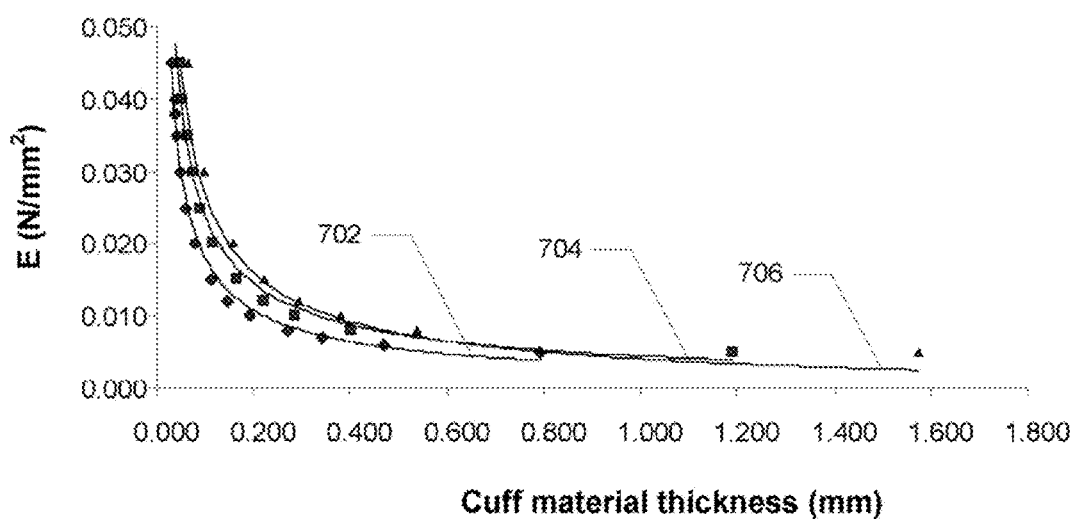
FIG. 7 is a graph summarizing safe combinations of Young's modulus and cuff thickness for producing cuff bodies for safe use on nerves of three different diameters.

The size and/or outside diameter of the nerve on which the electrode assembly is installed may further influence the selection of materials and dimensions to construct a cuff body with safe compliance characteristics, in particular with smaller nerve diameters. Below initial nerve diameters of about 2 mm, the compliance of all cuff body examples summarized in FIG. 6 fell outside of the safe compliance region 606 except for the cuff made of the hypothetical diamond-like polymer (line 612). As the size of the nerve decreases, the creation of a design that safely accommodates the anticipated 150% nerve swell may be particularly challenging. FIG. 7 is a summary of the combinations of Young's modulus (E) and cuff material thickness that accommodate a swelling of nerves to 150% of their initial size for nerves with initial diameters of 1.0 mm (line 702), 1.5 mm (line 704) and 2.0 mm (line 706). In each case, the combination of E and material thickness are mutually limited. Exceedingly thin walls are indicated for materials with higher Young's moduli, and exceedingly low Young's moduli are indicated for higher material thicknesses. In general, a combination of lower Young's moduli and thinner walls are likely to result in a cuff body design that may safely access the smaller nerves, as illustrated in FIG. 7.

In other aspects, the compliant properties of the cuff body 102 may be further influenced by additional factors including but not limited to the direction of loading of the cuff body 102, and the inclusion, placement and/or orientation of any reinforcing elements incorporated into the electrode assembly 100.

In an aspect, reinforcing elements may be incorporated into the electrode assembly 100 to provide a mechanically strong and protective element that is capable of withstanding forces applied to the cuff body 102 and/or forces transmitted to the cuff body 102 by the leads or electrodes during manufacture, implantation, nerve swelling and movement that would otherwise damage the compliant cuff body 102. These reinforcing elements are designed to provide enhanced strength and structural stability to the electrode assembly 100 without interfering with the compliant nature of the cuff body 102.

In an aspect, the cuff body 102 may be constructed using materials and dimensions such that the cuff body 102 may accommodate an increase in nerve radius of up to about 150% of the initial nerve radius with a reactive pressure of less than about 20 mm Hg. In another aspect, the electrode assembly 100 may further be designed to limit electrical noise and to facilitate the transmission of electrical signals to and/or from the nerve underlying the cuff body 102.

ii. Electrical Properties

In an aspect, the cuff body 102 of the electrode assembly 100 may completely enclose the nerve in a close-fitting and electrically insulating barrier which dynamically and continuously maintains the one or more electrodes 122 in close proximity to the underlying nerve. This close and continuous insulating barrier prevents unwanted signals from spreading into or out of the cuff body 102 in various nerve sensing or nerve stimulation applications. Further, the close apposition of the electrodes 122 to the nerve prevents unwanted signal attenuation between the electrodes and the underlying nerve.

For sensing applications, the low current spread and low signal attenuation achieved by the electrode assembly 100 in various aspects may improve the quality of nerve recordings by maximizing spatial selectivity and signal-to-noise ratio. For stimulation applications, the low spread and attenuation of electrical signals delivered by the electrode assembly 100 may decrease the voltage level required to reach stimulation threshold which may help to extend the battery life of an implanted stimulator, improve spatial selectivity, and minimize the potential for unintended stimulation of nearby nerves or muscles.

b. Components of Electrode Assembly

Referring back to FIG. 4, the electrode assembly 100 may include a cuff body 102 with an attached lead body 114 with at least one lead 120, one or more first closure elements 124 and second closure elements 126, and one or more electrodes 122. In an aspect, the cuff body 102 may be a sheet or tube built from a natural or synthetic elastomeric polymer material including, but not limited to: silicone, urethane, nylon, rubber, polyester, polyethylene, or any other known elastomeric polymer material. The electrode assembly 100 may further incorporate a reinforcing textile or other reinforcing element (not shown) such as a polymer formed into a strand, sheet, or fabric with a knitted, braided, woven, or felted construction.

i. Cuff Body

In various aspects, the electrode assembly 100 includes a cuff body 102 to hold the electrodes 122 in close proximity to the underlying nerve, to provide an insulating barrier to enhance the transmission of electrical signals to and/or from the underlying nerve, and to support the attached lead body 114. In an aspect, the unsealed cuff body 102 in its flat configuration is a generally rectangular sheet as illustrated in FIG. 4. In another aspect, the cuff body 102 includes an elastic material that is cast, stamped, extruded or otherwise formed into a tubular structure with a diameter similar to that of the nerve to which the electrode assembly 100 is to be installed. In an aspect, the elastic material included in the cuff body 102 may be a polymer including, but not limited to: a silicone rubber, a silicone adhesive dispersion, a urethane rubber or a urethane adhesive dispersion.

As discussed herein previously in connection with FIG. 6 and FIG. 7, a cuff body material having a predetermined elasticity, material thickness, and cuff body diameter may be designed in accordance with Eqn. (I) to create theoretically safe, but impractical cuff body designs. In order to achieve sufficient compliance of the cuff body, the material thicknesses may range from 1 pm to about 150 µm depending on the desired application and the elasticity of the material. Without reinforcement, the extremely thin cuff body material would be vulnerable to damage such as tearing during the manufacturing, handling, implantation, and/or bearing of electrodes during use of the cuff body. A cuff body constructed essentially of an unreinforced elastic polymer may be suitable for a limited number of functions including, but not limited to short-term testing applications in which the cuff body is isolated from internal or external loads. However, a compliant cuff body that incorporates one or more reinforcing elements may be better suited for other applications.

Reinforcing Elements

In an aspect, the electrode assembly may further include one or more reinforcing elements designed to protect the elastic materials of the cuff body from mechanical damage during manufacture, installation, and use. The placement and orientation of the one or more reinforcing elements may provide robust mechanical support for the elements of the electrode assembly during manufacture and installation, while permitting the cuff body to perform within a safe compliance region as illustrated in FIG. 6 and as described herein previously. In an aspect, the one or more reinforcing elements may protect the compliant cuff body from mechanical damage without interfering with the stretching of the cuff body, particularly in the context of accommodating nerve swelling and/or nerve movement as described herein previously.

The incorporation of the at least one reinforcing element in an aspect allows the construction and use of electrode assemblies that are sufficiently compliant to accommodate the swelling and/or movement of the nerve without imparting damage to the nerve in use and are additionally sufficiently robust to prevent mechanical damage to the electrode assembly during production, installation, and use. In another aspect, the inclusion of the one or more reinforcing elements in various aspects may provide an anchor 'island' for the attachment of electrodes and/or may provide reinforcement to reduce the potential of damage to the cuff body from external as well as internal loading to other electrode assembly components such as the lead body.

In yet another aspect, the at least one reinforcing element may affect cuff body compliance differently depending on the direction of a load applied to the cuff body and/or a region of the cuff body to which a load is applied. For example, the at least one reinforcing element may be designed to allow the cuff body to retain relatively compliant characteristics in a circumferential direction to protect the nerve against catastrophic pressure increases while simultaneously reinforcing a limited region of the cuff body to protect the one or more electrodes attached to the cuff body against potentially catastrophic external or internal loading conditions experienced during installation or use of the electrode assembly. In another non-limiting example, the electrode assembly may incorporate a number of non-compliant fibers oriented parallel to the longitudinal edges of the cuff body in order to reduce the longitudinal compliance of the cuff in order to resist elongation of the cuff along the length of the nerve during use, while maintaining relatively high circumferential compliance to permit a relatively high degree of elongation in the circumferential direction in response to relatively low forces to accommodate swelling and/or movement of the nerve without undue compression during use.

In one aspect, the choice of materials and architecture selected for use as reinforcing elements may result in a relatively non-deformable and non-compliant reinforcement. In other aspects, the reinforcing elements may function as a deformable but non-compliant reinforcement, or may function as a deformable and compliant reinforcement. The reinforcing elements may be situated in any location within, on, and/or around the cuff body and may be oriented in any one or more directions relative to the cuff body without limitation.

In one aspect, the one or more reinforcing elements may be provided in the form of a textile. Non-limiting examples of textile materials suitable for use as the one or more reinforcing elements include any natural or synthetic material such as polypropylene, polyester, polyethylene, polyamide, PTFE, PEEK, silk, or the like. In this aspect, the textile material may be intrinsically non-conductive or the textile material may be an intrinsically conductive material that may be electrically insulated with a deformable coating including but not limited to a natural or synthetic polymer such as silicone, urethane, nylon, rubber, polyester, polyethylene, or the like.

In one aspect, the reinforcing element may include a second polymer element distinct from the first polymer forming the cuff body. This reinforcing polymer element may be incorporated in any known form including but not limited to a particle, a strand, a sheet, a coating, or a fabric. Depending on the design and desired characteristics of the cuff body, the reinforcing polymer may have a lower, identical or higher elasticity relative to the elastic material of the cuff body. In various aspects, the reinforcing polymer may be bonded to the entire inner or outer surface of the cuff body, or the reinforcing polymer may be bonded to the cuff body at a number of discrete points. In various other aspects, the reinforcing polymer may be incorporated directly into the cuff body matrix to form a composite material. In yet other additional aspects, the reinforcing polymer may be an electrical insulator, or the reinforcing polymer may be an electrical conductor, for example an oxidatively doped conductive polymer material.

Discrete Reinforcing Elements

Figure 8:
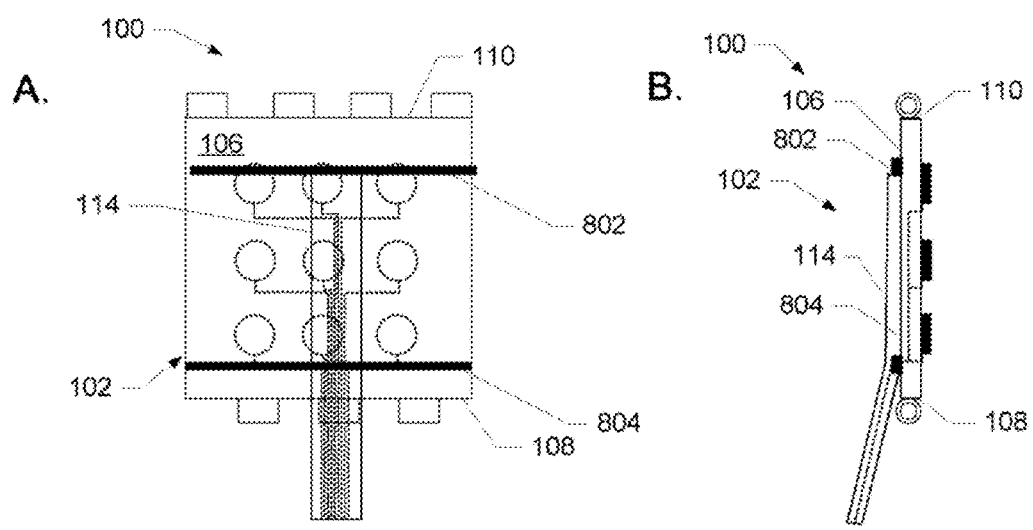
FIG. 8 is a side view (FIG. 8A), an end view (FIG. 8B) of a cuff body reinforced with a two strands of reinforcing material.

In applications where at least minimal internal or external loading forces and/or torques may be experienced by the cuff body, the addition of one or more discrete reinforcing elements may be indicated in an aspect. For example, one or more strands 802 of a textile or polymer reinforcing material oriented along the length of the cuff body 102 and parallel to the longitudinal edges 108 and 110, as illustrated in FIG. 8, may provide a suitable level of reinforcement for the electrode assembly 100. Reinforcement in the longitudinal orientation may permit the nerve to swell in a radial direction opposed only by the elastic material 804 of the cuff body 102, whereas a circumferential orientation of the single strand 802 relative to the nerve centerline would undesirably oppose compliant accommodation by the cuff body 102 during the time the nerve 202 swells. This reinforcing strand 802 may be added as an anchor strip for electrode or lead body attachment and/or as an access point for mechanically handling and manipulating the electrode assembly 100 in an aspect. In this aspect, the reinforcing strand 802 may prevent the electrodes and/or lead body from being torn from the cuff body 102 and/or to maintain the electrode spacing along the longitudinal axis of the electrode assembly 100.

Figure 9:
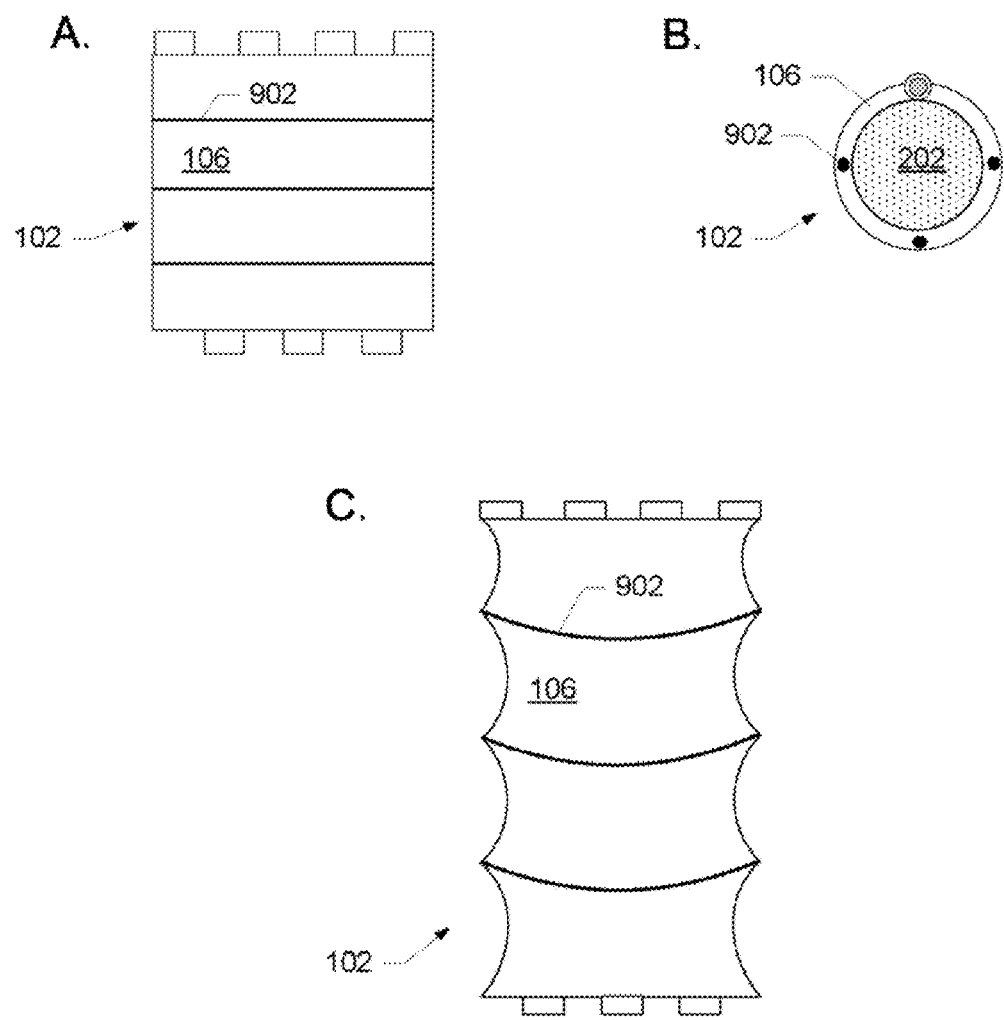
FIG. 9 is a top view (FIG. 9A) and an end view (FIG. 9B) of a cuff body reinforced with a three strands of reinforcing material.

In another aspect, the cuff body 102 may incorporate multiple discrete reinforcing elements, as illustrated in FIG. 9. FIG. 9A is a top view showing the three discrete reinforcing strands 902. In this aspect, the reinforcing elements are provided in the form of three strands 902 aligned along the longitudinal axis of the nerve 202 and distributed about the circumference of the cuff body 102 when installed on the nerve 202, as illustrated in the end view shown in FIG. 9B. The strands 902 may be attached to the outer surface 106 of the cuff body 102, or the strands may be embedded in the elastic material of the cuff body 102 as illustrated in FIG. 9B. In this aspect, the cuff body 102 is reinforced against stretching in the longitudinal direction, while maintaining a suitable level of compliance in the circumferential direction as illustrated in FIG. 9C; this circumferential compliance permits the cuff body 102 to accommodate the swelling and/or other movements of the nerve 202.

In various aspects, the number, shape, location, and orientation of reinforcing members may vary without limitation. In one aspect, the reinforcing elements may be arranged to provide a predetermined level of compliance in the circumferential direction to accommodate nerve swelling and nerve movements during use of the electrode assembly 100. In other aspects, the reinforcing elements may also be arranged to provide a predetermined level of compliance in other directions of loading including, but not limited to stretching or compressing the cuff body 102 along the longitudinal axis of the nerve, bending of the cuff body 102 in a direction perpendicular to the longitudinal axis of the nerve, torsion about the longitudinal axis of the nerve, and any combination thereof.

Figure 10:
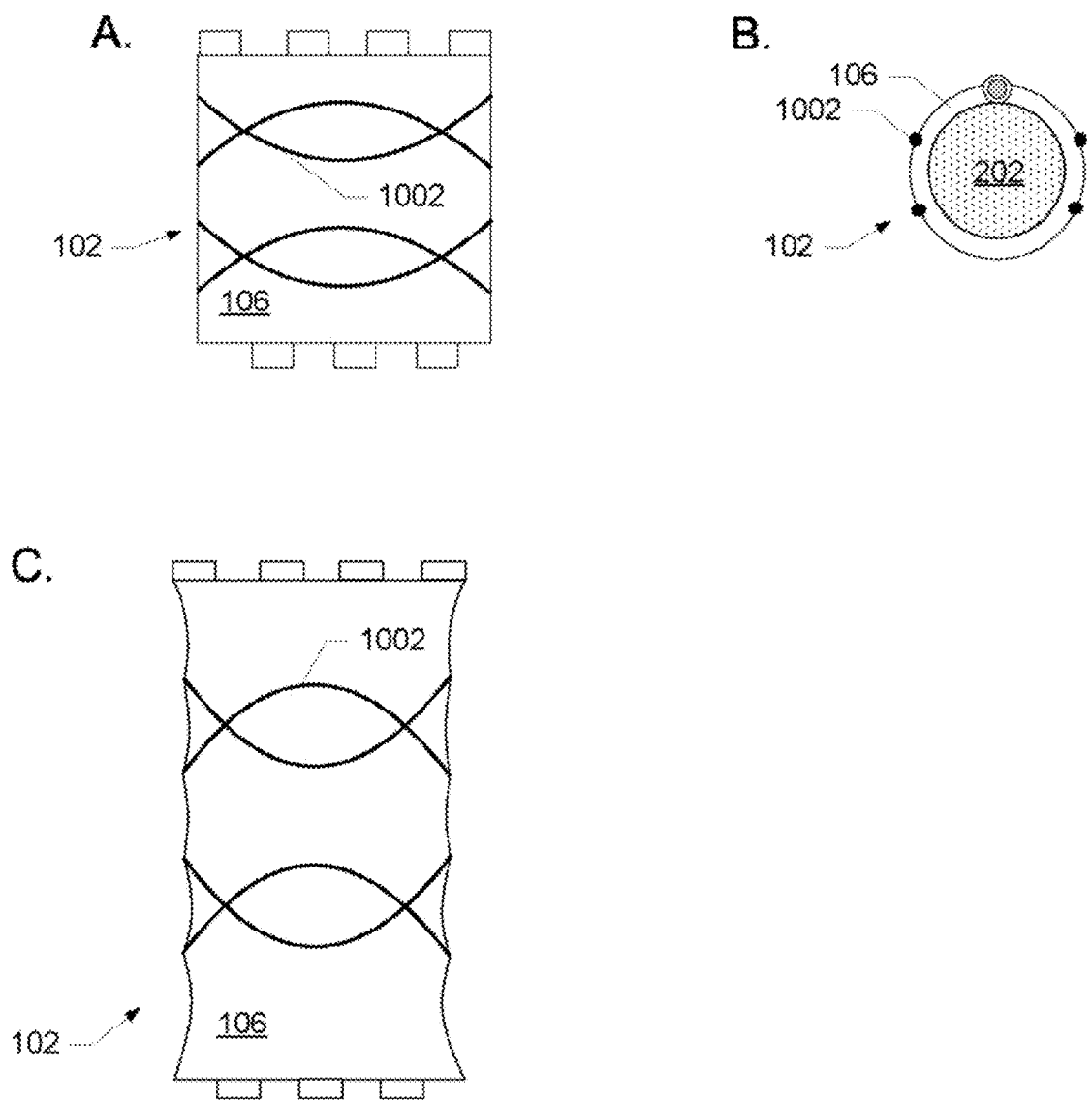
FIG. 10 is a top view (FIG. 10A) and an end view (FIG. 10B) of a cuff body reinforced with paired and curved strands of reinforcing material.

FIG. 10 is a top view (FIG. 10A) and an end view (FIG. 10B) of a reinforced cuff body 102 with alternating curved reinforcing elements 1002 that may be incorporated into the cuff body 102 in an aspect. In this aspect, the reinforcing elements 1002 reinforce the cuff body 102 along the longitudinal axis of the cuff body 102 in a manner similar to the cuff body 102 illustrated in FIG. 9, while still imparting circumferential compliance under circumferential loading, as illustrated in FIG. 10C. In addition, due to the curved shape of the reinforcing elements 1002, the cuff body 102 may maintain a degree of compliance in the longitudinal direction. As a result, the cuff body 102 may stretch or compress in the longitudinal direction, during the bending of the nerve for example, to serve one or more of the needs communicated in the paragraphs above in an aspect.

In another aspect, reinforcing elements may be incorporated into the cuff body 102 to provide linear circumferential compliance over a predetermined range of nerve swelling (i.e. within the safe compliance region 606 illustrated in FIG. 6) and additionally to provide a relatively non-compliant response to loading beyond this predetermined range of swelling. For example, a cuff body 102 in this aspect may be used in an application in which the reinforcement prevents catastrophic external loading from being transmitted to the electrodes.

Figure 11:
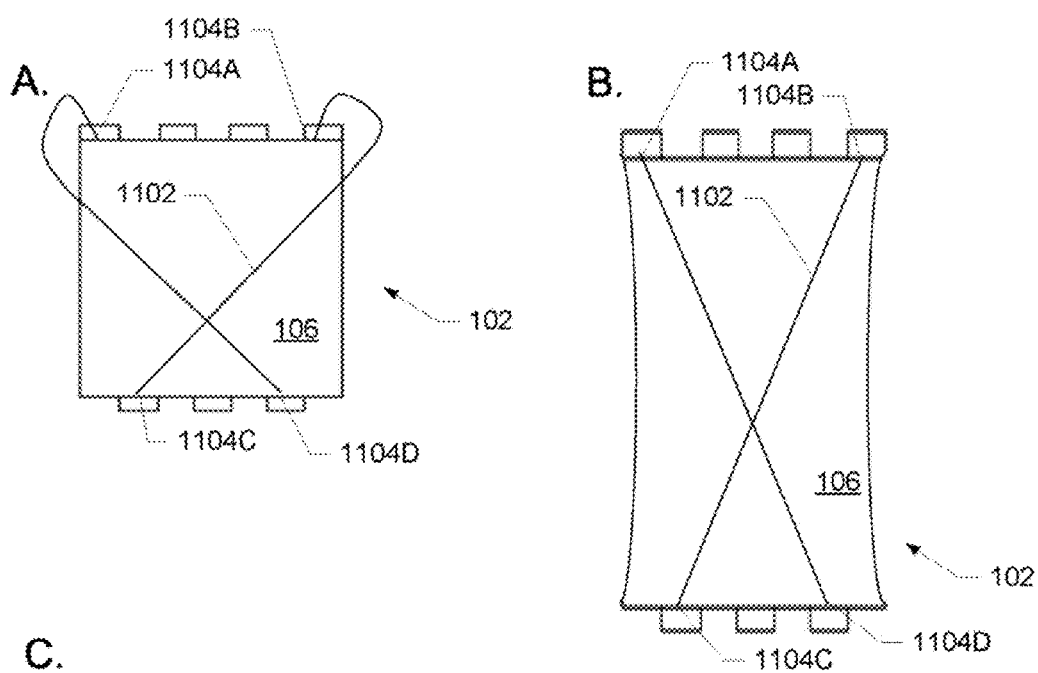
FIG. 11 is a top view of a cuff body reinforced with a pair of reinforcing strands in a resting (FIG. 11A) and stretched configuration (FIG. 11B)

FIG. 11A is a top view of a cuff body 102 incorporating a pair of reinforcing strands 1102 arranged diagonally across the outer surface 106 and anchored at four discrete points 1104A-D. In FIG. 11A, the reinforcing strands 1104A-D are shown in a relaxed state before any load is applied. FIG. 11B is another top view of the cuff body 102 with a sufficient circumferential force applied to fully load the reinforcing strands 1102. A schematic load/deflection curve summarizing the compliance characteristics of the cuff body 102 in this aspect is shown in FIG. 11C. At relatively low loads, corresponding to the forces exerted by a swelling nerve, the only contribution to the load/deflection curve comes from the compliant cuff body substrate and the resulting slope of the load/deflection curve is relatively shallow. At higher loadings, the load is resisted by the reinforcing strands 1102 in tandem with the elastic material of the cuff body 102 and no further deflection occurs if the reinforcing strands 1102 are sufficiently non-compliant. The point at which the reinforcing strands 1102 are fully extended and begin to carry the load is characterized by a point of inflection 1106 in the load/deflection graph. In an aspect, the cuff body 102 may incorporate reinforcing strands 1102 that are fully extended just after the nerve has swollen beyond 150% of its original diameter in order to operate within the safe compliance region 606 of FIG. 6.

Mesh Reinforcing Elements

In an aspect, the one or more reinforcing members may be provided in the form of a mesh reinforcing element such as a deformable textile that defines a plurality of openings throughout the mesh. Non-limiting examples of materials suitable for use as a mesh reinforcing element include a non-conductive polymeric mesh material such as an electrically-isolating polyester mesh and a surgical mesh. The surgical mesh material may be a woven fabric used in a variety of applications including chest wall reconstruction, strengthening tissues, providing support for internal organs, and treating surgical or traumatic wounds. Surgical meshes are typically composed of Gore-Tex®, Teflon®, polypropylene or some other polymer, and titanium-based meshes such as those used in some back surgeries. Non-limiting examples of surgical meshes include a commercially available Polymer Knit Mesh (PETKM) such as PETKM3002 or PETKM3003 (Textile Development Associates, Inc., Brookfield, Conn., USA). The PETKM 3002 typically has 1.0 mm pores and a weight of 34 g/m$^2$, while the PETKM 3003 typically has 2.0 mm pores and a weight of 14 g/m$^2$.

The reinforcing textile may be bonded to the cuff body 102 in any bonding pattern without limitation in various aspects. Non-limiting examples of suitable bonding patterns include bonding to an entire inner or outer surface of the cuff body 102, and bonding at a number of discrete points such as along both sides of the cuff seam adjacent to the closure elements. In an aspect, the reinforcing textile may be incorporated directly into the cuff body matrix to form a composite material. The reinforcing textile may be incorporated in this aspect as a strand, sheet, or fabric embedded in the uncured liquid cuff body matrix and cured to form a composite material.

In various aspects, the cuff body 102 may not possess sufficient local strength to resist the applied internal or external loads experienced during manufacture, implantation and/or use without breaking, tearing, irreversibly deforming, or otherwise structurally failing. In addition to providing overall reinforcement to the cuff body 102, the mesh reinforcing elements, especially in the regions in which the reinforcing textile is bonded to the elastic material of the cuff body 102, may provide a reinforced region upon which electrodes, a lead body, or any other associated element of the electrode assembly 100 may be mounted in various aspects.

The reinforcing textile may be oriented in any one or more directions relative to the cuff body 102 without limitation. For example, randomly oriented textile reinforcing fibers may be suspended in an uncured liquid polymer matrix and cured into a sheet or tube used in cuff body construction in an aspect. In another aspect, the reinforcing textile may be an anisotropic material in which the reinforcing material has a first load-to-elongation ratio along a first loading axis and a second load-to-elongation ratio along the second loading axis, where the second load-to-elongation ratio is lower than the first load-to-elongation ratio. In an aspect, the anisotropic material may be oriented in the cuff body 102 such that the cuff body 102 maintains suitable compliance in the circumferential direction to accommodate nerve swelling, while providing robust reinforcement in the longitudinal direction.

FIG. 12A is an end view of a cuff body 102 that is reinforced with a reinforcing textile sheet 1202 in an aspect. As illustrated in FIG. 12A, the reinforcing textile sheet 1202 may be anchored to the outer surface 106 of the cuff body 102 along two longitudinal seams 1204 and 1206. In this aspect, the reinforcing textile sheet 1202 may function mechanically in parallel with the compliant cuff body 102. The materials and dimensions of the cuff body 102 create a compliant structure that safely accommodates a 50% increase in diameter, but which may be too fragile on its own to be used in surgical applications. The reinforcing textile sheet 1202 forms a more robust, but oversized outer wall that acts as a reinforcing element for the fragile closed cuff body 102, as illustrated in FIG. 12B. In this aspect, the reinforcing textile sheet 1202 protects the compliant cuff body 102 from any damage that may occur during manipulation, manufacture, implantation, or body motion in use. The reinforcing textile sheet 1202 may further provide a mounting surface for electrodes and leads in another aspect. In this aspect, the reinforcing textile sheet 1202 may bear any forces applied to the lead and electrode and protect the compliant cuff body 102 from these external applied forces. In an additional aspect, the reinforcing textile sheet 1202 may form an outer layer with an inner diameter that is about 150% of the initial diameter of the cuff body 102 when installed as shown in FIG. 12B.

Figure 12:
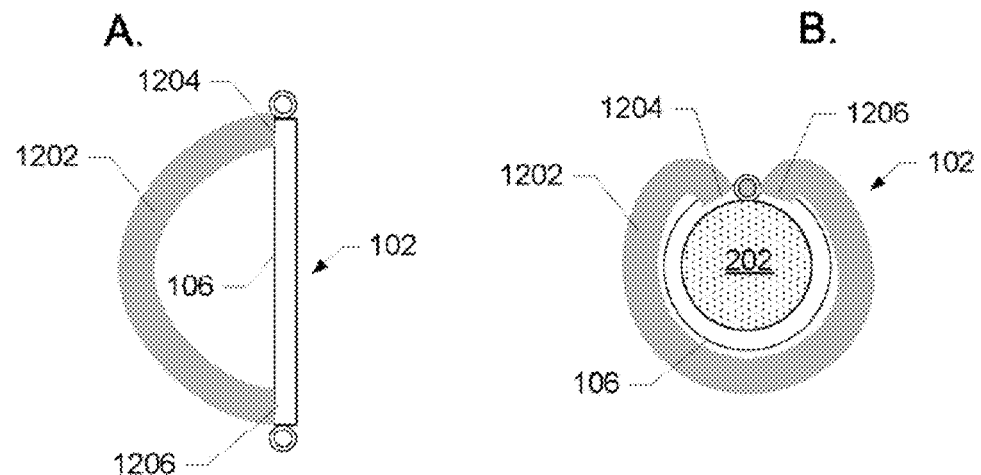
FIG. 12 is an end view of a cuff body reinforced with a reinforcing sheet attached at two edges in a flat (FIG. 12A) and a tubular (FIG. 12B) configuration.

In the aspect illustrated in FIG. 12, the material properties, dimensions, and anchoring pattern of the reinforcing textile sheet 1202 are sufficient to allow the cuff body 102 to remain safely compliant up to the nerve damage threshold. Sizing the reinforcing textile sheet 1202 to be 150% of the cuff body 102 circumference provides for cuff body mechanics that are safely compliant up to nerve swelling of 150% of the original nerve diameter. The reinforcing textile sheet 1202 acts primarily to protect the cuff body 102 and to simultaneously permit the compliant properties of the cuff body 102 to be realized without damaging the nerve.

FIGS. 13A-B are end views of another reinforcement scheme similar to the reinforcement scheme shown in FIG. 12 in another aspect. In this aspect, the reinforcing textile sheet 1302 is anchored to the outer surface 106 of the cuff body 102 along a third seam 1308 in addition to two longitudinal seams 1304 and 1306. This additional connection point of the reinforcement to the cuff body 102 offers an additional reinforcement island or additional location upon which to securely mount electrodes and/or the lead body to the electrode assembly 100. Similar to the aspect illustrated in FIG. 12, the reinforcing textile sheet 1302 is designed to allow the compliant cuff body 102 to change shape with changes in nerve diameter, shape, or with body movement, while simultaneously providing a stable mount for electrodes and leads and providing a robust outer surface that mechanically protects the inner, compliant, thin-walled cuff body 102.

Figure 13:
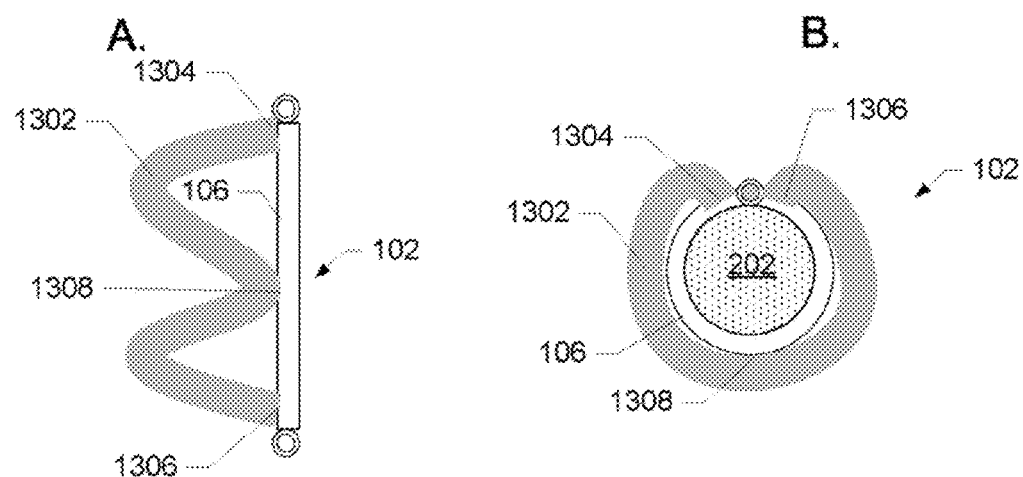
FIG. 13 is an end view of a cuff body reinforced with a reinforcing sheet attached at three edges in a flat (FIG. 13A) and a tubular (FIG. 13B) configuration.

The reinforcing textile sheets 1202 and 1302 illustrated in FIGS. 12 and 13 may be either non-compliant or compliant. The use of reinforcing elements that are also compliant may allow the use of reinforcing textile sheets that are less than 150% of the initial cuff body circumference, such that the combined compliance of the reinforcing textile sheet and cuff body allows for nerve swelling up to 150% of the original nerve diameter with less than 20 mm Hg of compression by the cuff body 102.

In an aspect, a compliant reinforcing textile sheet, such as a mesh, may be essentially the same length as the cuff body circumference and may further be fully bonded to the cuff body 102, eliminating any gaps between the outer surface of the cuff body 102 and the contacting surface of the reinforcement. FIGS. 14A and 14B are top and end views, respectively, of a cuff body 102 in which a reinforcing sheet 1402 is bonded to the outer surface 106 of the cuff body 102 in an aspect. The cuff body 102 is shown installed on a nerve 202 in FIG. 14C. In this aspect, the reinforcing sheet 1402 forms a reinforced protective cover over the entire outer surface 106 of the cuff body 102. This reinforcing sheet 1402 further provides for the attachment of electrodes, lead bodies, and any other element associated with the electrode assembly 100; these additional elements may be situated anywhere on this reinforcing outer layer. In another aspect, the reinforcing sheet 1402 may be bonded to the inner surface of the cuff body 102.

Internal Reinforcing Elements

Figure 15:
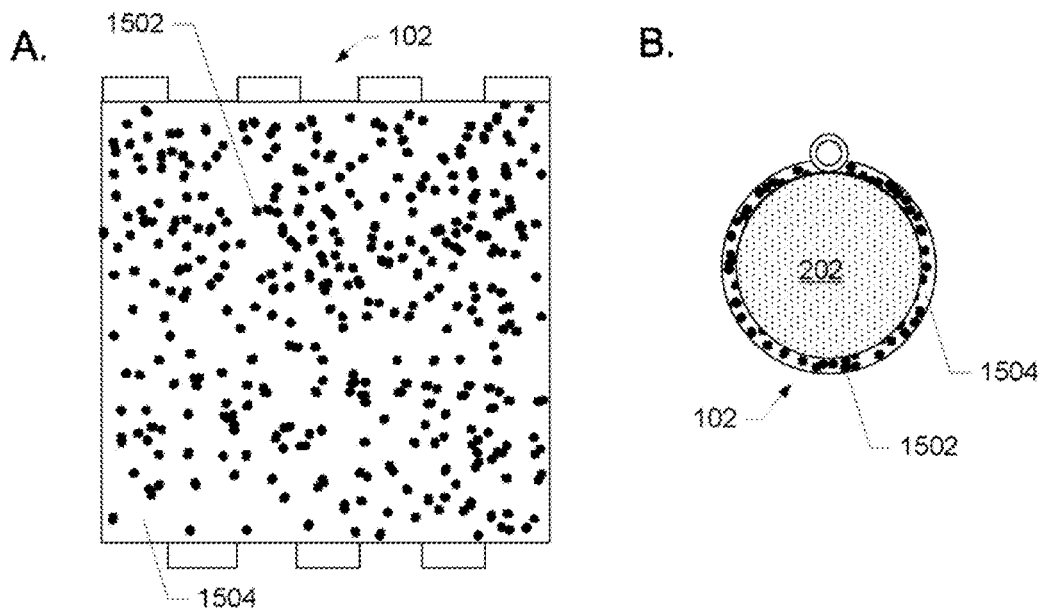
FIG. 15 is a top view (FIG. 15A) in a flat configuration and an end view (FIG. 15B) in a tubular configuration of a cuff body reinforced with randomly distributed reinforcing particles.

In another aspect, the one or more reinforcing elements may be bonded within the elastic material of the cuff body 102. FIG. 15A is a top view of a cuff body 102 with a plurality of internal reinforcing elements in the form of reinforcing particles 1502 bonded within the elastic material 1504 of the cuff body 102. In this aspect, the internal reinforcement design combines the advantages of the highly elastic cuff body material with the mechanical properties of a stronger and less elastic reinforcing material. In this aspect, the reinforcing particles 1502 may be suspended at random within a precured liquid matrix material and subsequently cured in place. The cuff body 102 in this aspect is shown installed on a nerve 202 in FIG. 15B. The overall compliant nature of the cuff body 102 is maintained by allowing the elastic material 1504 to stretch along the multiple free paths between the reinforcing particles 1502. On a larger scale, the reinforcing particles 1502 provide enhanced strength and stability during the production, installation, and use of the electrode assembly 100 by distributing forces across the plurality of reinforcing particles 1502.

Figure 16:
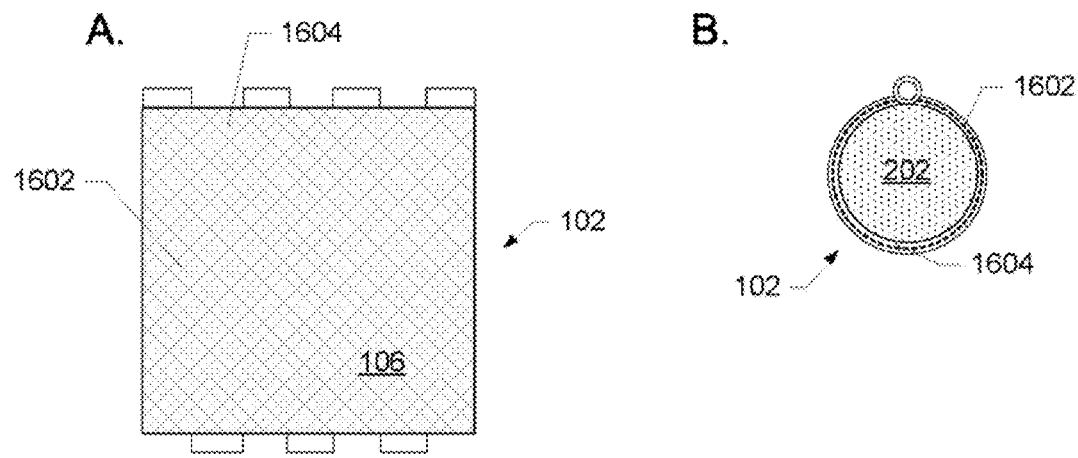
FIG. 16 is a top view (FIG. 16A) in a flat configuration and an end view (FIG. 16B) in a tubular configuration of a cuff body reinforced with an embedded reinforcing sheet.

FIGS. 16A and 16B are top and end views, respectively, of a cuff body 102 with a reinforcing sheet 1602 embedded within the elastic material 1604 of the cuff body 102 in an aspect. The embedded reinforcing sheet 1602 may contain any of the reinforcing materials described herein previously such as a polymer sheet or a reinforcing textile material. In this aspect, the reinforcing sheet 1602 embedded in the elastic material 1604 is designed to provide the benefits of the elastic material of the cuff body in addition to the benefits of the reinforcement.

Figure 17:
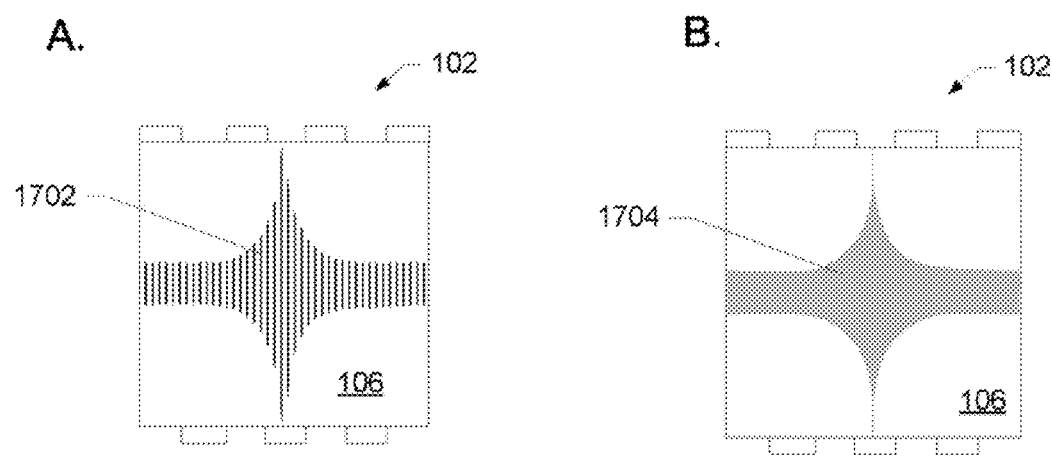
FIG. 17A and FIG. 17B are top views of a cuff body reinforced with a reinforcing polymer.
Figure 18:
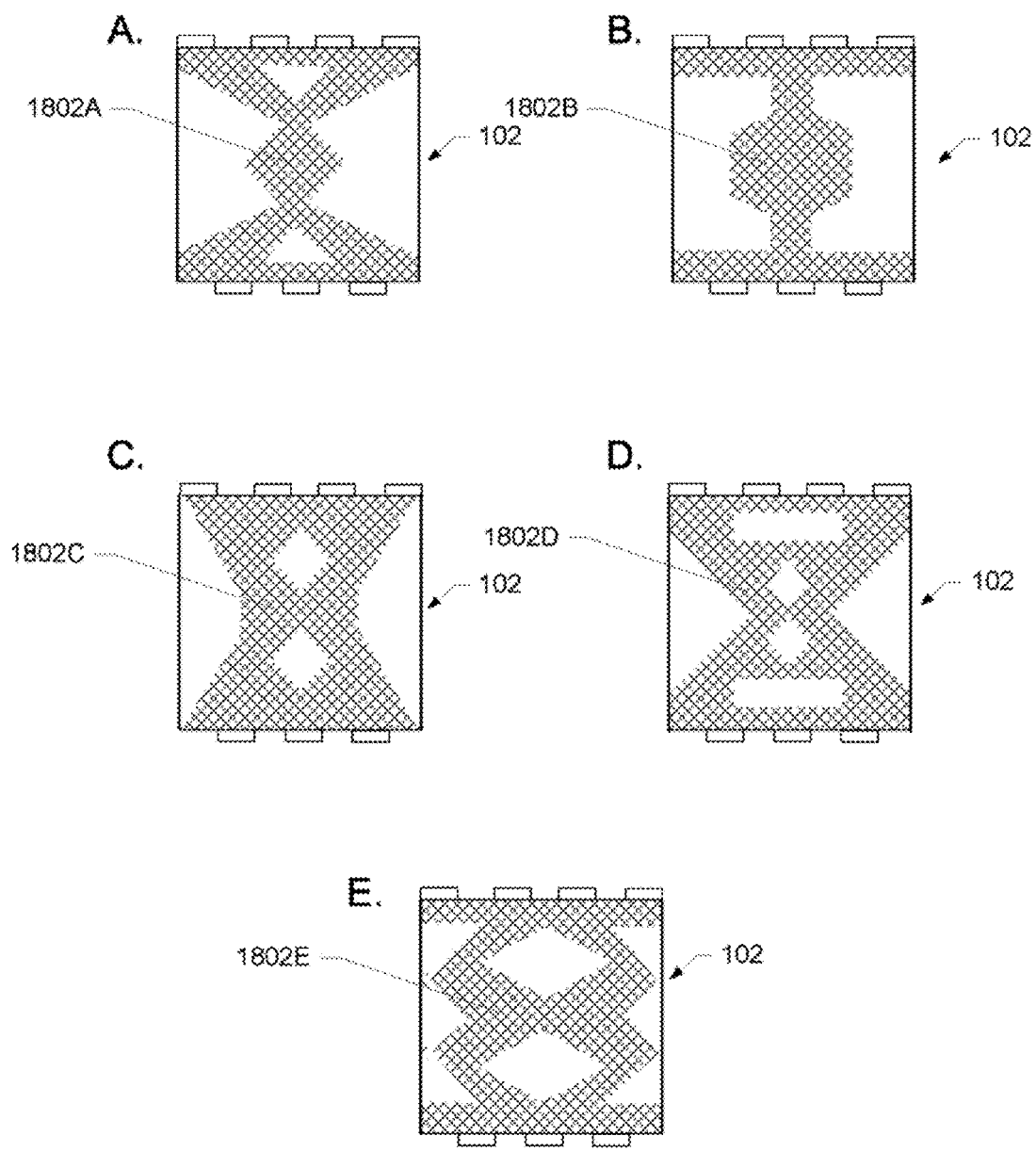
FIGS. 18A-E are top views of cuff bodies reinforced with reinforcing polymer materials in various patterns.

In still another aspect, the reinforcement may be a second polymer material poured and cured into depressions, grooves, and/or any other voids created in the elastic material of the cuff body. Non-limiting examples of suitable locations for reinforcement using the second polymer material in this aspect include the outer surface of the cuff body, the inner surface of the cuff body, within the elastic material of the cuff body, and any combination thereof. FIG. 17A is a top view of a cuff body 102 in one aspect that is reinforced by a plurality of discrete polymer reinforcing elements 1702 bonded into grooves or channels formed in the outer surface 106 of the cuff body 102. In this aspect, the shape of the combined footprint of the polymer reinforcing elements 1702 is designed to provide a mounting substrate for electrodes along the longitudinal axis of the enclosed nerve; the parabolic profile of the footprint on the circumferential axis is designed to provide a gradually increasing resistance to deformation in the vicinity of the mounting site of the electrodes as well as maintaining a degree of compliance along the longitudinal axis. In this aspect, the reinforcing polymer may be poured into channels or other depressions or voids previously cut or cast into a desired shape and depth within the elastic material of the cuff body 102 and then cured in place. In another aspect, illustrated in FIG. 17B, the reinforcing polymer may be cast as a single continuous structure 1704 in a depression or void of predetermined size and shape formed in the elastic material of the cuff body 102. FIGS. 18A-E illustrate alternative patterns of reinforcing polymer materials 1802A-E, respectively, in various aspects of the cuff body 102.

In various other aspects, the reinforcing polymer may be fully bonded to a surface of the cuff body 102, embedded within the elastic material of the cuff body 102, and/or painted on a surface of the cuff body 102. In yet another aspect, the one or more reinforcing elements may be provided in the form of a conductive polymer material, described herein previously, arranged into a prefabricated circuitry configuration; the prefabricated circuitry may be bonded to or embedded within the elastic material of the cuff body 102 as described in any of the aspects described herein.

Figure 19:
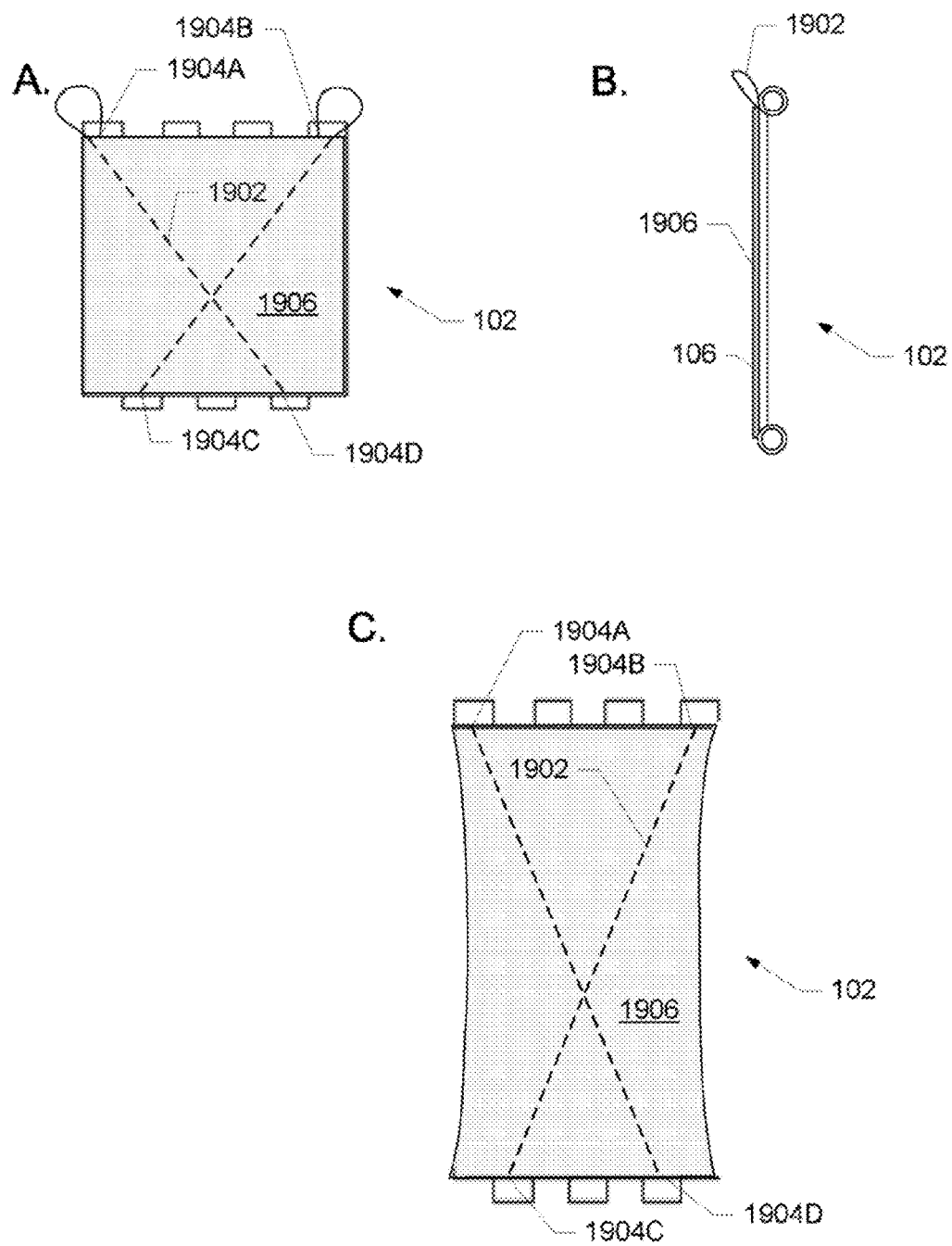
FIG. 19 is a top view (FIG. 19A) and an end view (FIG. 19B) of a cuff body reinforced with an embedded pair of reinforcing strands in a resting configuration.

In another additional aspect, a reinforcing polymer may be bonded over discrete reinforcing strands. FIG. 19 is a top view (FIG. 19A) and a side view (FIG. 19B) of this additional aspect of the cuff body 102, as well as a top view (FIG. 19C) of this cuff body stretched in response to a circumferential load. As illustrated in FIG. 19, diagonal reinforcing strands 1902 attached to the cuff at attachment points 1904A-D may be incorporated into the cuff body 102 to impart an abrupt change in the compliance of the cuff in response to loading in the circumferential direction beyond a predetermined degree of stretching, in a manner similar to the aspect described herein previously in connection in FIG. 11. Referring back to FIG. 19, a reinforcing polymer sheet 1906 covers the diagonal reinforcing strands 1902; this reinforcing polymer sheet 1906 is attached to the cuff body 102 at its outermost edges. In this aspect, the reinforcing polymer sheet 1906 is attached to the cuff body 102 in such a way that any additional frictional forces due to the movement of the diagonal reinforcing strands 1902 relative to the reinforcing polymer sheet 1906 are minimal.

Coated Mesh Materials

Figure 20:
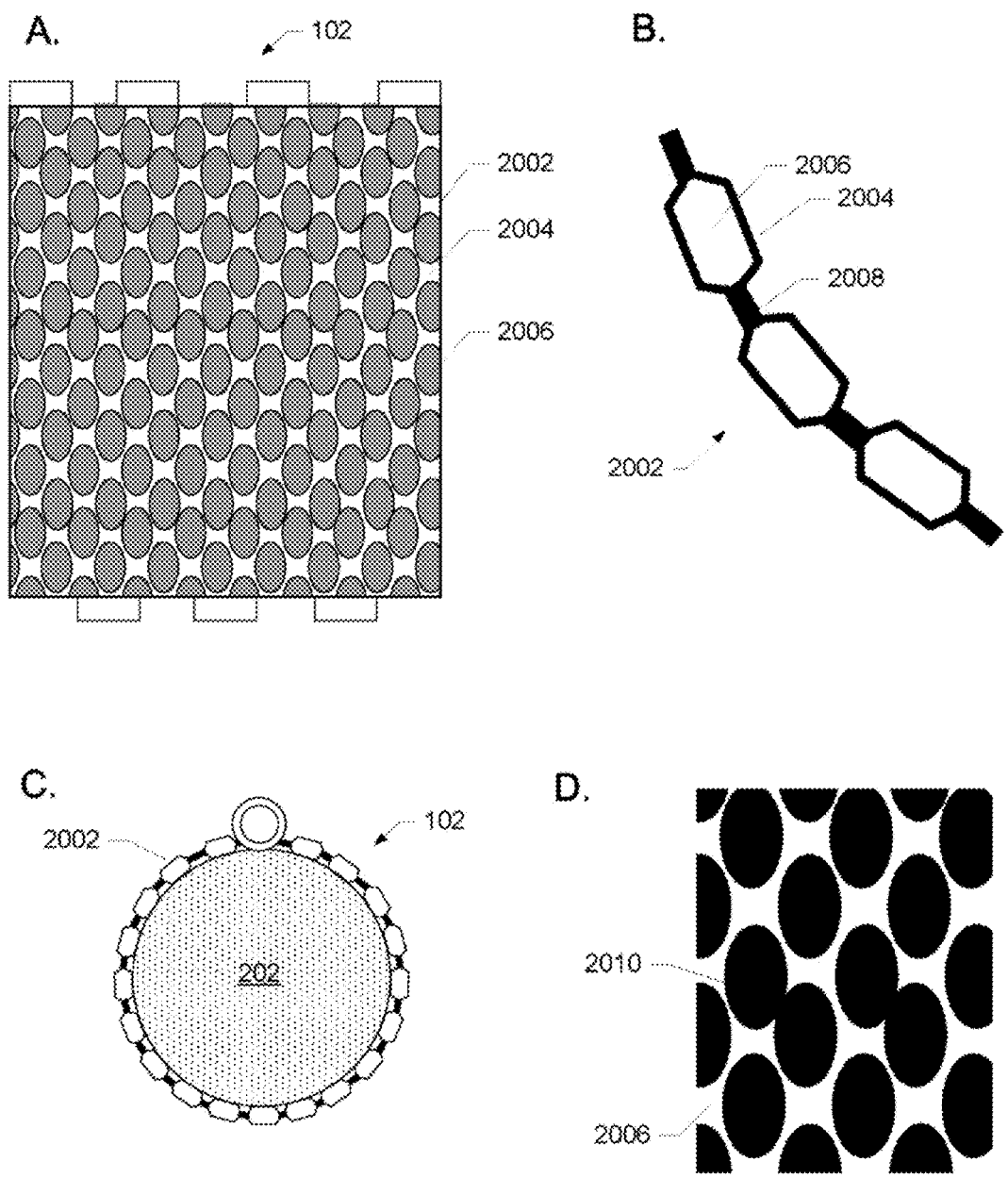
FIG. 20 is a top view (FIG. 20A) in a flat configuration and an end view (FIG. 20B) in a tubular configuration of a cuff body formed from a coated deformable mesh material.

In various aspects, the cuff body 102 of the electrode assembly 100 may be provided in the form of a compliant film of elastomer material situated over a compliant mesh reinforcement material and spanning the openings defined within the mesh material. Any suitable mesh material may be used as reinforcement including, but not limited to, any of the surgical meshes and textile reinforcing materials described herein previously. FIG. 20A is a top view of a cuff body 102 formed from a reinforced elastomer material 2002. FIG. 20B is a close-up cross-sectional view of a segment of the reinforced elastomer material 2002. The reinforced elastomer material 2002 includes a thin film 2004 of an elastomer material such as silicone rubber, creating a continuous covering of the mesh reinforcement material 2006 and spanning the openings 2008 defined within the mesh material. The resulting composite of elastomer and reinforcement mesh materials may then be formed into a tubular structure that defines a central lumen to receive the nerve 202 as illustrated in FIG. 20B.

As shown in FIG. 20D, the mesh reinforcement material 2006 defines a plurality of openings 2010 throughout the mesh. The mechanics of the mesh reinforcement material 2006 are influenced by the dimensions of the plurality of openings 2010. By manipulating the geometry and size of the mesh openings 2010, such as width to height ratio and/or the relative size and density of the openings 2010 within the mesh, the mesh reinforcement material 2006 may impart with differing compliance characteristics to the cuff body 102 along perpendicular loading axes. To avoid compression injury to a nerve, a cuff body 102 including the reinforced mesh material 2006 may possess sufficient compliance along an axis that will define the circumferential axis of the cuff body 102 when it is in place around a nerve; this circumferential compliance may be higher than the compliance of the cuff body 102 along the longitudinal axis of the nerve.

Figure 21:
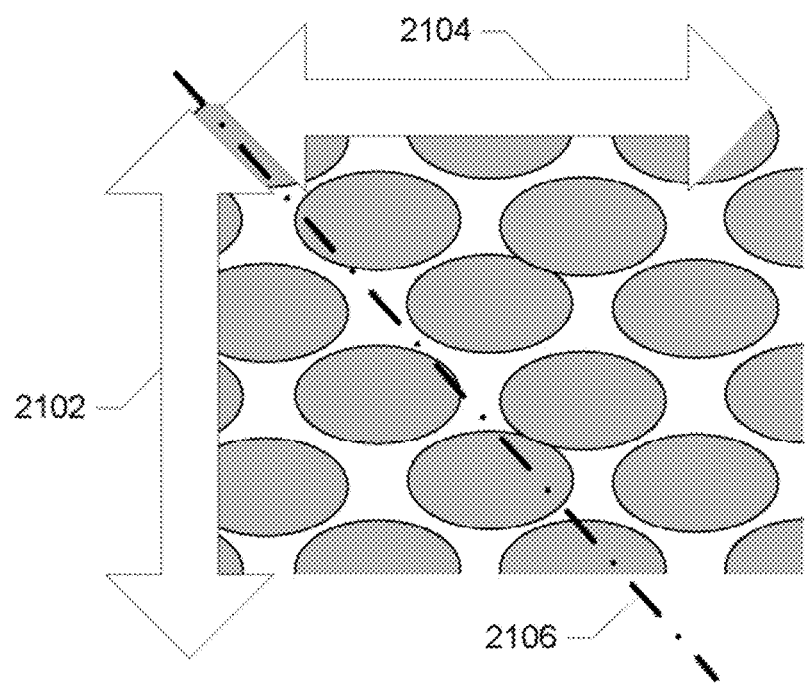
FIG. 21 is a top view of a deformable mesh material illustrating the compliant and non-compliant axes.

As illustrated in FIG. 21, the mesh material may have a compliant axis 2102 and a non-compliant axis 2104 in an aspect. In another aspect, the mesh material may have a relatively more compliant axis and a relatively less compliant axis. In various other aspects, the mesh material may impart varying degrees of compliance to the cuff body 102 in numerous directions. The geometry, size, and density of the mesh openings may be selected according to at least one of a number of factors readily assessed by one of skill in the art, including but not limited to the size and location of the nerve, and the quality and stability of electrical contact needed in the particular application.

If the less compliant or non-compliant axis 2104 of the mesh reinforcement material 2006 is oriented along the longitudinal axis of the cuff body 102, the more compliant axis 2102 which has a relatively low load to elongation ratio will also be oriented in an appropriate direction for accommodating the expected post-operation swelling of the nerve in an aspect. In this aspect, if the electrodes are aligned along the non-compliant axis 2104 of the mesh reinforcement material 2006, the longitudinal spacing between electrodes may be maintained, as this axis is less likely to elongate or deform.

Referring back to FIG. 21, the mesh material may be oriented along an axis 2106 that bisects the right angle formed between the compliant axis 2102 and the non-compliant axis 2104 of the mesh reinforcement material 2006 in an aspect. When formed into a tubular or cylindrical structure, the mesh reinforcement material 2006 is thus oriented such that the cuff body 102 possesses various degrees of compliance in multiple dimensions along and around nerve and the axis.

In another aspect, a textile reinforcing mesh with repeating cells in which the cells are identical to each other or individually customized may be incorporated into the cuff body 102 to provide a higher level of protection against predetermined loadings that tend to tear the electrodes from the cuff body 102 of the electrode assembly 100. The repeating cell configuration in this aspect provides the option of configuring a final electrode assembly 100 with compliance characteristics that are considerably different along different axes. The geometry, orientation and location of the textile reinforcing mesh in this aspect may be manipulated to influence structural integrity of the electrode assembly 100, in particular the cuff body 102, under preselected loading conditions. For example, the textile reinforcing mesh may be selected to yield linear compliance characteristics for a predetermined range and/or direction of loading and may further be selected to abruptly transition to a non-compliant condition beyond the predetermined load range and/or outside the predetermined direction of loading in an aspect.

Load-deflection testing using standard engineering and/or materials science methods may be conducted to confirm that any of the reinforcement configurations described herein are likely to avoid exerting any discernable effect on the compliance of the cuff body 102 up to the targeted 50% deflection. For example, the safety of any of the reinforcement configurations described herein above may be verified empirically using for example an Instron machine to apply a force equivalent to a radial pressure of 20 mm Hg and verify a deflection of at least 50% of the original length of the cuff body 102.

ii. Electrodes and Lead Body

Referring back to FIG. 4, the electrode assembly 100 may include one or more electrodes 122 attached to the cuff body 102 and exposed on the inner surface 104. The one or more electrodes 122 may be electrically connected to one or more leads 120 attached to the cuff body 102 via a lead body 114 in an aspect. In another aspect, the leads 120 may be woven or otherwise enter the inside of the cuff body 102 through an opening formed in the material of the cuff body 120; the leads 120 may function directly as the one or more electrodes 122 on the inner surface 104 of the cuff body.

The one or more electrodes 122 may establish electrical communication between an external measuring and/or stimulation device (not shown) and the nerve in an aspect. In this aspect, the one or more electrodes 122 may deliver an electric signal, such as a current or voltage pulse, to the nerve. The one or more electrodes 122 may also measure an electric signal propagating through the nerve and/or a characteristic of the nerve/electrode interface, such as the electrode impedance.

Figure 22:
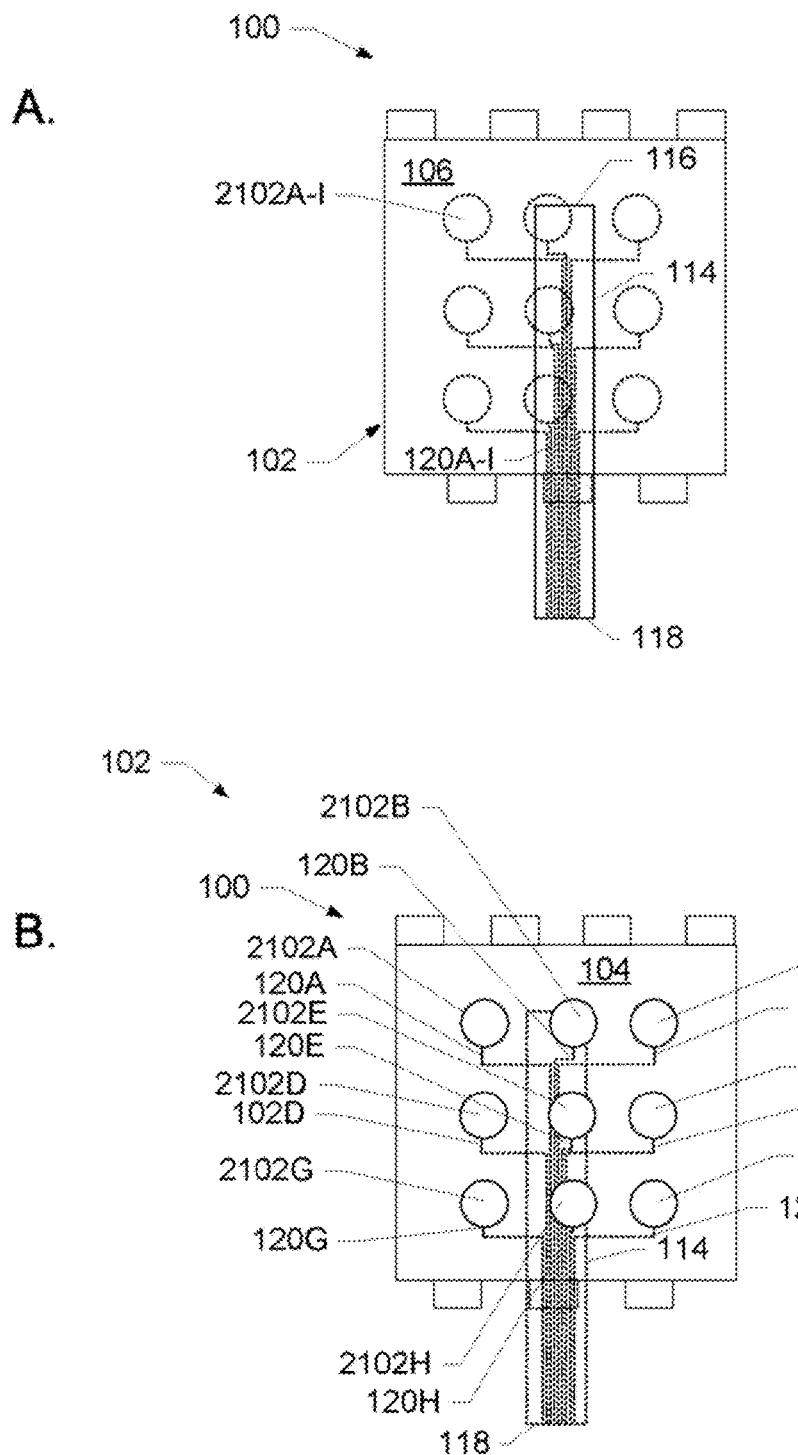
FIG. 22 is a top view of the outer surface (FIG. 22A) and inner surface (FIG. 22B) of the electrodes and leads of the electrode assembly.

FIG. 22 is a top view (FIG. 22A), and a bottom views (FIG. 22B) of the electrode assembly 100 in two aspects. As shown in FIG. 22A, the leads 120A-I may penetrate the material of the cuff body 102 along an attached portion 116 of a lead body 114 and pass from the outer surface 106 to the inner surface 104 of the cuff body 102. In an aspect, the leads 120A-I may be embedded within the material of the cuff body 102 and/or the lead body 114. The materials of the cuff body 102 and/or the lead body 114 may provide insulation to the leads 120A-I during use. In another aspect, the leads 120A-I may be embedded within the lead body 114, and exposed on the inner surface 104 of the cuff body 102.

As shown in FIG. 22B, the electrodes 2012A-I may be attached to the ends of the leads 120A-I. In one aspect, the electrodes 2102A-I may be connected to leads 120A-120I, respectively and arranged in an array with rows parallel to the longitudinal axis of the nerve and columns perpendicular to the longitudinal axis of the nerve, as illustrated in FIG. 22B. In other aspects, the electrodes may be arranged parallel to the longitudinal axis of the nerve only, perpendicular to the longitudinal axis of the nerve only, or in any other spatial arrangement without limitation.

In various aspects, the electrodes and leads may include any wire, foil or other biocompatible electrically conductive material suitable for carrying electrical signals. Non-limiting examples of suitable biocompatible electrically conductive materials include biocompatible metals and alloys such as platinum, iridium, stainless steel, indium tin oxide, and gold; carbon nanostructures such as carbon nanotubes and carbon nanofilaments; intrinsically or oxidatively doped conductive polymers such as polyanilines, polythiophenes and polypyrroles; and anisotropic conductive composites of non-conductive polymers such as silicone rubbers, silicone adhesive dispersions, urethane rubbers, or urethane adhesive dispersions that further contain dispersed conductive particles such as any of the biocompatible metals and alloys or carbon nanostructures described herein previously.

In an aspect, the electrodes and/or leads may be provided in the form of mechanically non-compliant, metallic electrodes and leads capable of providing reinforcement to the cuff body. In this aspect, the dimensions and orientation of the electrodes and/or leads may be specified in part to modify the degree of compliance of the electrode assembly in one or more directions including, but not limited to, the longitudinal, circumferential, and/or radial directions. For example, if the non-compliant electrodes are oriented along the longitudinal axis of the cuff body, the incorporation of the electrodes may result in a reduction in the compliance of the electrode assembly in the longitudinal direction.

In an aspect, the electrodes and leads may be provided in the form of mechanically compliant electrodes and leads capable of stretching to accommodate nerve swelling or movement during use of the electrode assembly. In one aspect, these compliant electrodes and leads may include conductive polymer-filled channels created in the cuff body by casting or cutting channels into the inner surface of the cuff body, filling the channels with an uncured elastic conductive polymer such as an oxidatively doped conductive polymer, and curing the elastic conductive polymer in place. The conductive polymer may then be entirely or selectively insulated from the inner and/or outer surfaces of the cuff body using a non-conductive polymer, such as the compliant polymer comprising the cuff body, to form a combination of uninsulated electrodes and/or insulated leads.

Figure 23:
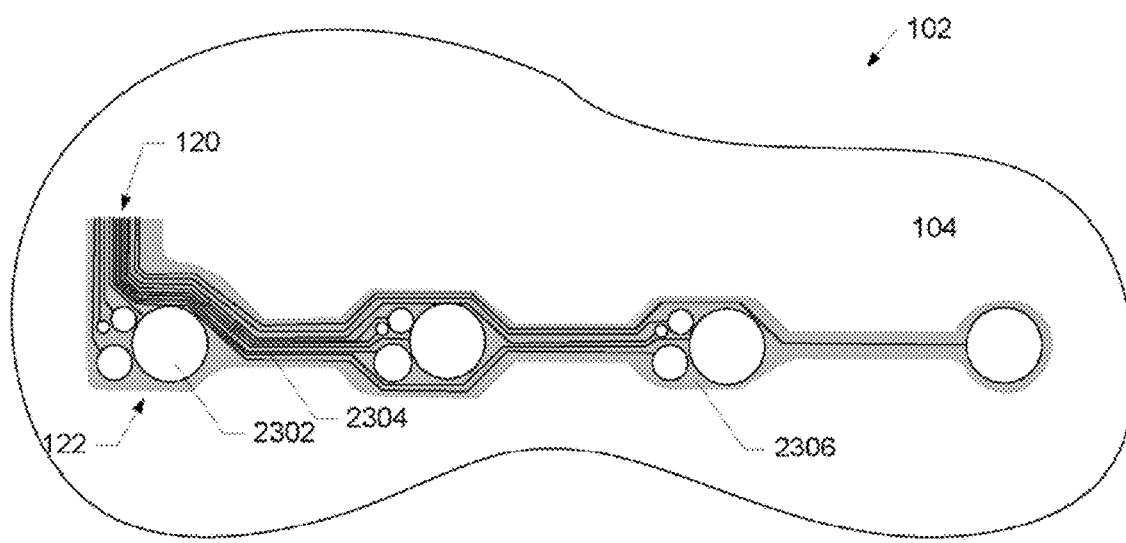
FIG. 23 is a top view of a multiple electrodes mounted on an inner surface of an electrode assembly.

In another aspect, the electrode assembly 100 may include multiple electrodes and leads, as illustrated in FIG. 23 in a close-up bottom view. In this aspect, the electrodes 122 and leads 120 may be provided in the form of mechanically compliant, polymer-based electrodes 2302 and leads 2304 capable of stretching in response to nerve swelling or movement during use of the electrode assembly 100. In this aspect, the polymer-based electrodes 2302 and leads 2304 may be entirely or selectively insulated from the inner surface 104 and/or outer surface 106 of the cuff body 102 using a non-conductive polymer 2306.

Figure 24:
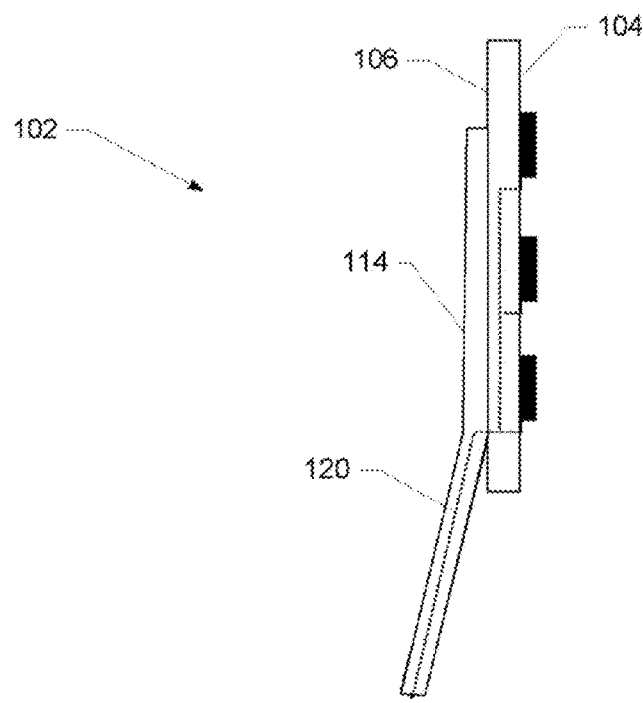
FIG. 24 is a cross-sectional end view of an electrode assembly.

Referring back to FIG. 4, the electrode assembly 100 may further include a lead body 114 housing the leads 120 that is attached to the cuff body 102. A cross-sectional view of the lead body and cuff body 102 is illustrated in FIG. 24. In an aspect, the lead body 114 into which the conductive leads 120 are embedded may be a reinforced compliant structure with architecture and materials similar those used in the reinforced compliant cuff body 102. In another aspect, the lead body 114 may be a reinforced compliant structure with architecture and materials distinct from those of the cuff body 102. In yet another aspect, the lead body 114 may be a deformable but non-compliant structure. The lead body 114 may possess compliant and/or deformable characteristics, so that the cuff body 102 is protected from forces applied through mechanical coupling of the cuff body 102 to the lead body 114. In another aspect, the lead body 114 may be mounted any of the reinforced regions described herein previously.

In the aspect illustrated in FIG. 24, the lead body 114 may have a compliant design that may further be reinforced using any of the one or more reinforcing elements described herein above. The leads 120 may be attached to or embedded within the lead body 114. The attached end of the lead body 114 may be attached to the outer surface 106 of the cuff body essentially at the region at which the leads 120 pass from the outer surface 106 to the inner surface 104 of the cuff body 102. The material of the lead body 114 may provide additional structure to withstand various internal and/or external forces resulting from the interaction of the leads 120 with the cuff body 102, and function as a stress relief. In an aspect, the lead body 114 may be a discrete structure that is attached to the outer surface 106 of the cuff body 102 at its attached end 116. In another aspect, the lead body may be formed or molded from the same material as the cuff body 102 and may form a continuous integrated structure.

iii. Closure Elements

In various aspects, the electrode assembly may include one or more closure elements. Referring back to FIG. 4, the first and second closure elements 124 and 126 may be situated along the first and second longitudinal edges 108 and 110 of the cuff body 102. When the cuff body 102 is installed by wrapping the inner surface 104 of the cuff body 102 around the nerve 202, as illustrated in FIG. 5B, for example, the closure elements 124 and 126 may mechanically interlock to secure the first and second longitudinal edges 108 and 110 in an aligned and adjacent orientation, forming a closed cuff body 102 containing the nerve 292 in the lumen formed by the inner surface 104 of the cuff body 102.

Figure 5:
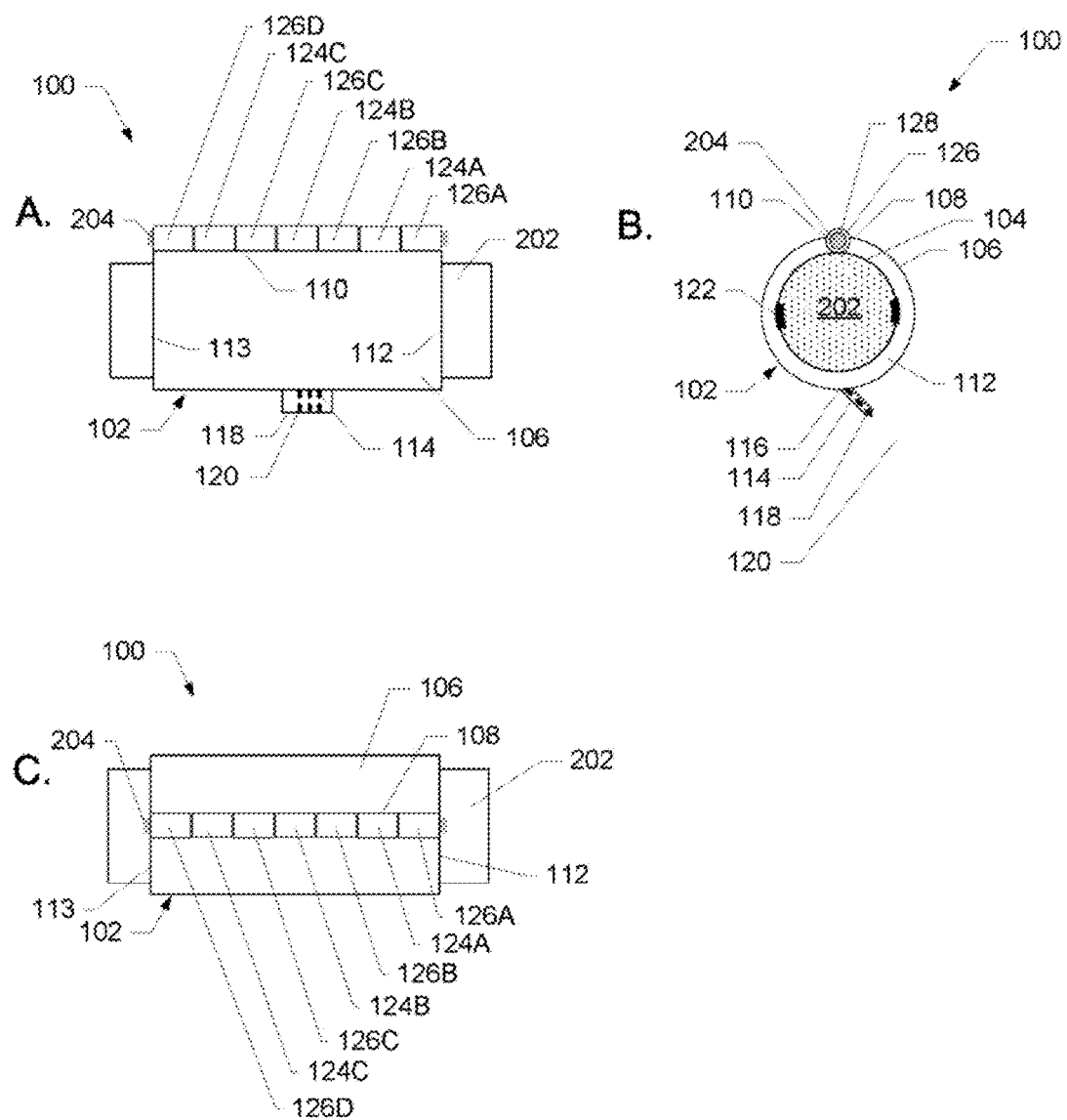
FIG. 5 is a side view (FIG. 5A), an end view (FIG. 5B), and a top view (FIG. 5C) of a cuff body situated around a longitudinal segment of a nerve.

The closure elements may be any suitable bio-compatible closure elements capable of securing the longitudinal edges 108 and 110 to maintain the tubular structure of the closed cuff body 102 during the use of the electrode assembly 100. As a non-limiting example, the first and second closure elements 124 and 126 as illustrated in FIGS. 4-5 and described previously herein, may be a series of hollow cylindrical structures affixed to the opposing first and second longitudinal edges 108 and 110, respectively in an alternating manner. In this aspect, when the cuff body 102 is wrapped around the nerve 202, as illustrated in FIG. 5, the first and second closure elements 124 and 126 align to form an elongated hollow cylinder, similar to the knuckles of a hinge. In this aspect, a deformable pin 204 may be inserted through the aligned lumens within the hollow cylindrical structures of the first and second closure elements 124 and 126. The deformable pin 204 holds the alternating closure elements 124 and 126 in position, thereby preventing the cuff body 102 from unintentionally reverting to its unsecured planar orientation. The deformable pin 204 may be an elongate cylindrical element formed from a bio-compatible material into a deformable and/or compliant structure.

The closure elements may be separate structural elements that are attached to the material forming the longitudinal edges 108 and 110 of the cuff body 102 in an aspect. In this aspect, the closure elements may be affixed to the elastic material of the cuff body 102 and/or any of the one of more reinforcing elements situated adjacent to the longitudinal edges 108 and 110 of the cuff body 102. In another aspects, the closure elements may be formed from a material that is the same as the elastic material of the cuff body 102, from a material that is the same as the material of the one of more reinforcing elements, or from a material that is different from either the elastic material of the cuff body 102 or the one or more reinforcing elements. In yet another aspect, the closure elements are formed as a continuous and integral structure with the cuff body 102 using the same elastic material and/or materials of the one or more reinforcing elements.

In another additional aspect, the closure elements may be similar to the closure elements of the nerve cuff described in U.S. Pat. No. 8,214,056. which is hereby incorporated by reference in its entirety.

II. Method of Producing Electrode Assembly

Figure 25:
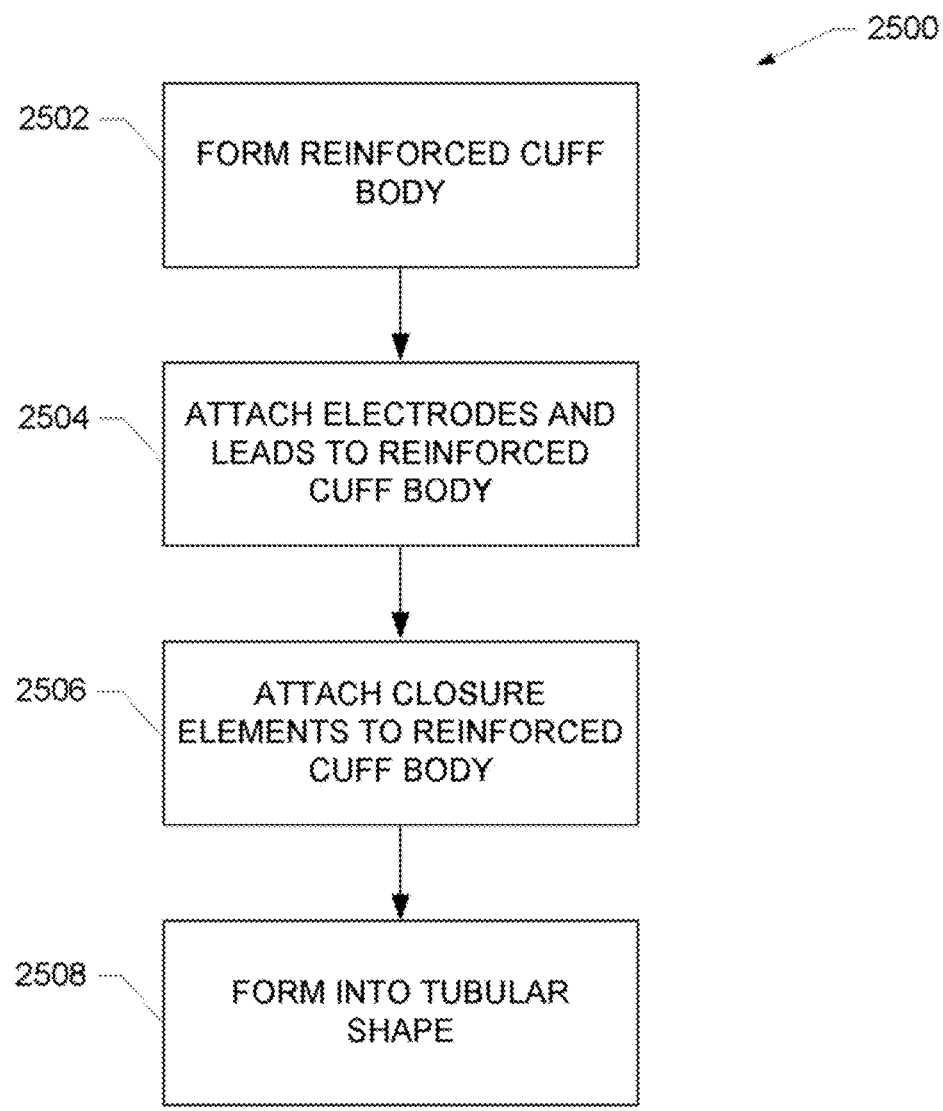
FIG. 25 is a flow chart illustrating a method of producing an electrode assembly.

In another aspect, a method of producing an electrode assembly that includes a reinforced, compliant cuff body is provided. FIG. 25 is a flowchart summarizing a method 2500 for manufacturing an electrode assembly in an aspect. A reinforced cuff body may be formed at step 2502. This reinforced cuff body may be a cuff body according to any of the aspects described herein above that may include an elastic material and one or more reinforcing elements. The electrodes and associated leads may be attached to the reinforced cuff body at step 2504, and the closure elements may be attached at step 2506. The electrode assembly may be formed into a tubular shape at step 2508.

a. Formation of Reinforced Cuff Body

Figure 26:
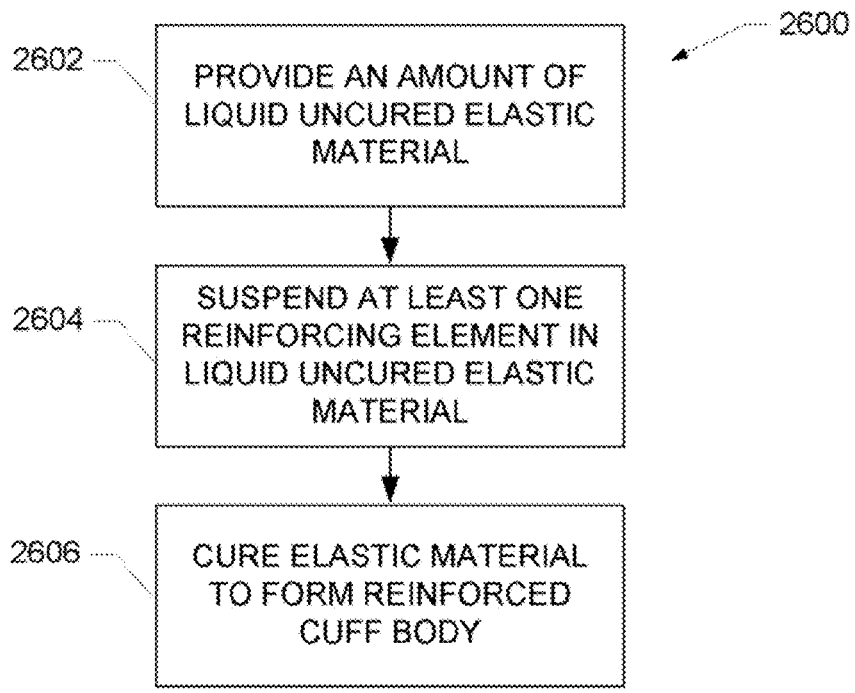
FIG. 26 is a flow chart illustrating a method of producing a reinforced cuff body in one aspect.

In various aspects, the reinforced cuff body may be formed at step 2502 using a variety of methods. In one aspect, the method 2500 of manufacturing an electrode assembly may include suspending the one or more reinforcing elements in a liquid uncured elastic material, and then curing the elastic material to a solid elastic material with the one or more reinforcing elements suspended therein. FIG. 26 is a flowchart summarizing a method 2600 of forming a reinforced cuff body in one aspect. An amount of uncured elastic material may be provided at step 2602, and the at least one reinforcing elements may be suspended in the uncured elastic material at step 2604. The elastic material may be cured at step 2606 to form a compliant nerve curve that additionally includes the at least one reinforcing element embedded within the cured elastic material.

The at least one reinforcing element may be any one or more of the reinforcing elements described herein previously including, but not limited to reinforcing particles, reinforcing strands or fibers, reinforcing sheets, reinforcing fabrics and any combination thereof. The one or more reinforcing elements may be suspended at any orientation without limitation including, but not limited to, a random orientation. For example, randomly oriented particles of cured reinforcing polymer may be suspended in an uncured liquid cuff body polymer matrix and cured into a sheet or tube to be used in cuff body construction. As another non-limiting example, one or more reinforcing fibers may be suspended within the uncured liquid cuff body polymer matrix aligned along the longitudinal axis of the cuff body and cured in place; in this example, the one or more reinforcing fibers may resist stretching of the cuff body along the length of the underlying nerve in use, while permitting the stretching of the cuff body in the circumferential direction. Various aspects of reinforcing elements such as reinforcing meshes, as well as orientations of the reinforcing elements, are described in detail herein previously.

Figure 27:
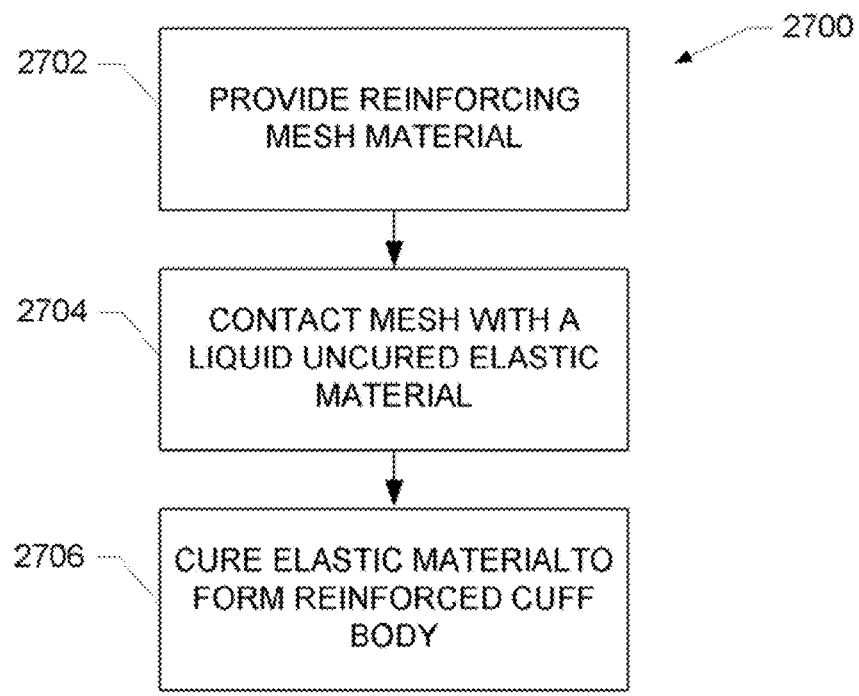
FIG. 27 is a flow chart illustrating a method of producing a reinforced cuff body in another aspect.

Referring back to FIG. 25, the reinforced cuff body may be formed at step 2502 by coating a reinforcing mesh material with a liquid uncured elastic material, and curing the elastic material to form the reinforced cuff body in an aspect. FIG. 27 is a flow chart illustrating a method 2700 of producing of a coated reinforcing mesh material in this aspect. A reinforcing mesh material is provided at step 2702 and coated with a liquid uncured elastic material at step 2704. The elastic material is cured at step 2706 to produce the reinforced cuff body material.

The reinforcing mesh material may be any of the reinforcing mesh materials described herein previously. As described previously, a plurality of openings may be defined throughout the reinforcing mesh material. In an aspect, the liquid uncured elastic material may form a film across the openings within the mesh at step 2704 that is cured into place at step 2706. To facilitate the contact of the liquid uncured elastic material with the reinforcing mesh material, the reinforcing mesh material may be reversibly fastened to a support fixture including, but not limited to, a support frame, a support rod, or any other known support fixture without limitation. Typically, the support fixture may fasten to the reinforcing mesh material around the periphery of the reinforcing mesh material well outside of the region to be used in the construction of the cuff body.

The reinforcing mesh material may be contacted with the liquid uncured elastic material using any known method of contacting an uncured liquid polymer with a mesh-like material without limitation, so long as a film of the uncured liquid polymer is formed over the opening within the reinforcing mesh material. Non-limiting examples of methods suitable for contacting the liquid uncured elastic material with the reinforcing mesh material include: pouring the uncured polymer over the mesh, brushing or rolling the uncured polymer over the mesh, spraying the uncured polymer over the mesh, and dipping the mesh into a pool of the uncured polymer.

For example, the liquid uncured elastic material may be suspended as a film across a plurality of openings defined by a textile reinforcing mesh and then cured into the reinforced cuff body. In one aspect, the film formed across the plurality of openings defined by the reinforcing mesh material may have a thickness of less than about 0.125 mm. For example, a film formed across the plurality of openings using a silicone adhesive dispersion may have a thickness ranging from about 0.050 mm to about 0.075 mm. In an additional aspect, the film may have a thickness of about 50% of the thickness of the filaments of the reinforcing mesh material. The elastic material may be any of the elastic materials described herein previously including, but not limited to: a silicone rubber, a silicone adhesive dispersion, a urethane rubber, or a urethane adhesive dispersion.

Figure 14:
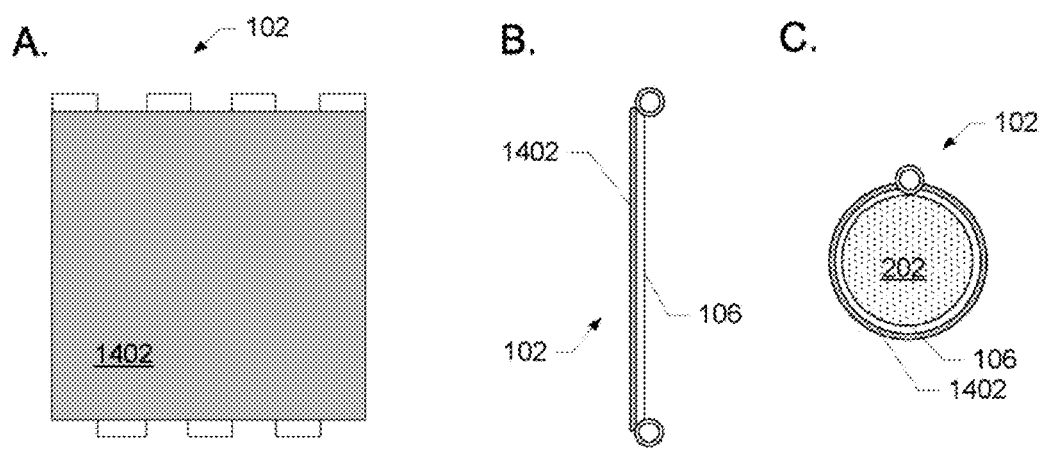
FIG. 14 is a top view (FIG. 14A) and an end view (FIG. 14B) of a cuff body reinforced with a bonded sheet of reinforcing material.
Figure 28:
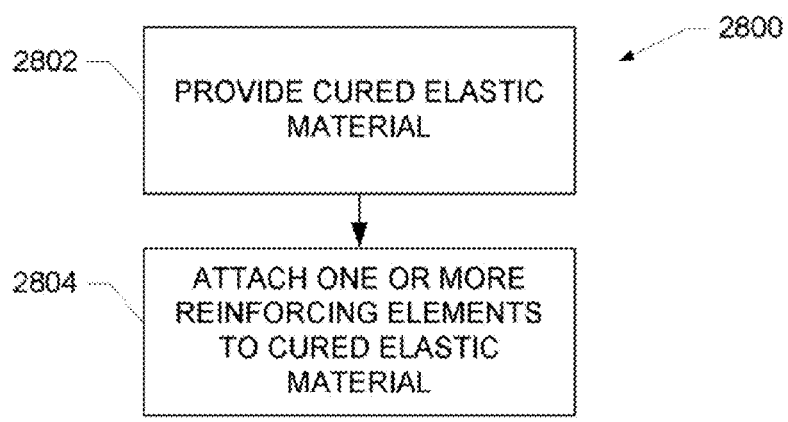
FIG. 28 is a flow chart illustrating a method of producing a reinforced cuff body in an additional aspect

As illustrated in the flow chart of a reinforced cuff production method 2800 provided in FIG. 28, the reinforced cuff body may be formed by providing a cured elastic material at step 2802 and attaching one or more reinforcing elements to the pre-cured elastic material of the cuff body at step 2804. Any of the one or more reinforcing elements described previously herein may be attached to the cured elastic material at any orientation in this aspect. For example, one or more discrete reinforcing fibers may be attached to the exterior surface of the elastic material and aligned along the longitudinal axis of the cuff body as described herein previously and as illustrated in FIGS. 8-9. In other non-limiting examples, a relatively inextensible reinforcing sheet may be attached to the elastic material at two or more finite points as described herein previously and illustrated in FIGS. 12-13, or a relatively compliant reinforcing sheet may be attached to an entire surface of the elastic material as illustrated in FIG. 14.

In yet another non-limiting example, the one or more reinforcing elements may be provided in the form of an uncured liquid reinforcing polymer that is brushed, painted, sprayed, or otherwise applied to the cured elastic material and subsequently cured. The uncured liquid reinforcing polymer may be poured and cured into channels or similar voids formed in the surface of the cured elastic material in an aspect, as described herein previously and illustrated in FIGS. 17-18. The grooves or channels may be cut or cast into a desired shape and depth within the cured elastic cuff body material, using any known method including, but not limited to: mechanical cutting, laser cutting, "soft lithography" casting techniques, and any combination thereof. For example, uncured liquid reinforcing polymer may be poured and cured into a grid of shallow channels formed in the outer surface of the cuff body.

In another aspect, the grooves may be formed into the inner surface of the cuff body and the reinforcing polymer may be provided in the form of an electrical conductor such as an oxidatively doped conductive polymer material. In this aspect, the conductive polymer may function as a conductive electrode and/or an insulated conductive trace and/or lead within the electrode assembly.

In yet another aspect, the liquid uncured reinforcing polymer may be injected into the cured elastic material of the cuff body. The reinforcing polymer may then be cured to provide a reinforcing polymer of a desired shape and depth embedded in the elastic cuff body material. In an additional aspect, the injected reinforcing polymer may be an electrical conductor such as an oxidatively doped conductive polymer material that may function as an insulated conductive trace or lead in the electrode assembly.

In another additional aspect, one or more reinforcing elements may be placed or affixed onto a base sheet of cured elastic material, followed by pouring a layer of uncured liquid elastic material to a desired thickness and curing the resulting composite cuff body material. The resulting composite cuff body material is as illustrated as FIG. 16 and described herein previously in one aspect. In this aspect, the base sheet may be formed to a thickness of about 50% of the desired total thickness of the cuff body composite material.

Referring back to FIG. 25, the method 2500 may further include may further include trimming the reinforced cuff body material formed by any of the preceding methods and aspects to a desired size at step 2502 in an aspect.

b. Attachment of Electrodes and Leads

The leads and electrodes attached to the reinforced cuff body may be any of the leads and electrodes described herein previously and illustrated in FIGS. 22-24. The electrodes may be attached using any known biocompatible adhesive. In an aspect, an amount of uncured elastic polymer material may be applied to the inner surface and/or electrode prior to placing the electrode on the inner surface, and the elastic polymer material may then be cured to attach the electrode. In other aspects, conductive polymer materials may be used to form the electrodes and/or leads on the inner surface and/or within channels or recesses formed within the material of the inner surface. In other aspects, the electrodes may be cast into the uncured liquid polymer cuff body material and subsequently cured in place.

In another aspect, the method 2600 may further include attaching a lead body reinforcement to the reinforced cuff body to provide mechanical support and reinforcement for the leads entering the reinforced cuff body. Any of the cuff body reinforcements described herein previously and illustrated in FIGS. 8-20 may be attached to the reinforced cuff body. The lead body itself may be formed using the same reinforced composite design used to construct the reinforced cuff body. In one aspect, the lead body may be formed separately from the reinforced cuff body and attached in a separate process. In another aspect, the lead body may be integral with the reinforced cuff body and may therefore be formed along with the reinforced cuff body in the same process.

c. Attachment of Closure Elements

Figure 29:
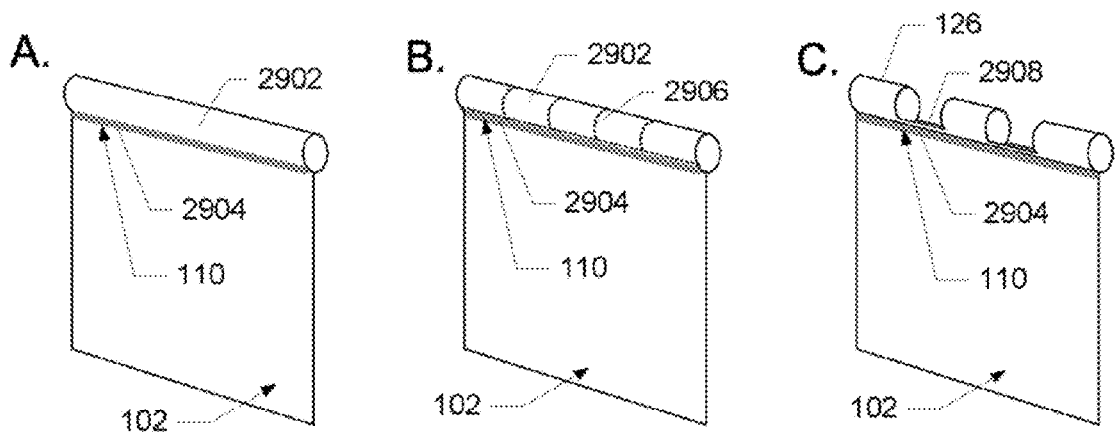
FIG. 29A-C are perspective views illustrating a method of producing closure elements for a cuff body.

The closure elements attached to the reinforced cuff body may be any of the closure elements described previously herein. In one aspect, illustrated in FIG. 29A, silicone rubber tubing 2902 may be affixed to a longitudinal edge 110 of the reinforced cuff body 102 using a deformable and biocompatible adhesive 2904. For example, a commercially available heat curable adhesive (NUSIL MED2-4213, NuSil Technology LLC, Carpinteria, Calif., USA) may be used as the adhesive. The hinge-like alternating closure elements 126 illustrated in FIG. 29C may be formed by cutting away segments of the adhered silicone rubber tubing 2902 along the cut lines 2906 shown as dashed lines in FIG. 29B. In an aspect, the longitudinal section of the silicone tubing 2902 may be retained as a reinforcing spine 2908 for the closure elements 126. In an aspect, the reinforcing spine 2908 may increase the surface area contacting the adhesive 2904 and may further bridge between any discrete reinforcing elements that may terminate along the longitudinal edge 110. In other aspects, the closure elements 126 may be provided in the form of discrete cylindrical elements with no reinforcing spine, and may further be adhered to the longitudinal edge individually.

III. Method of Using Electrode Assembly

Figure 30:
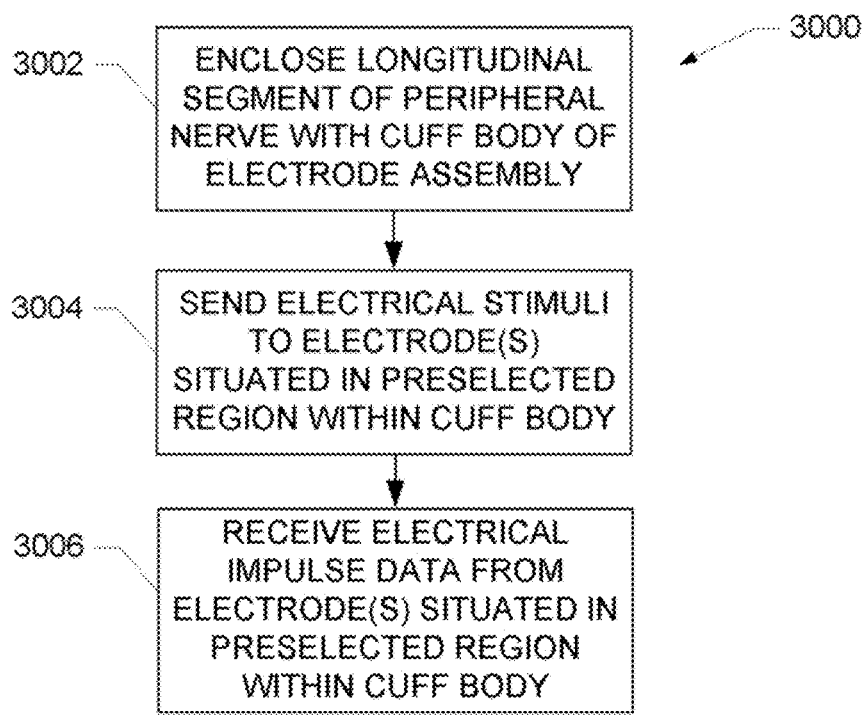
FIG. 30 is a flow chart illustrating a method of using an electrode assembly.

In various aspects, a method of using the electrode assembly described previously herein to record or stimulate electrical activity in a biological structure such as a peripheral nerve is provided. FIG. 30 is a flowchart depicting a method 3000 for using the electrode assembly in an aspect. In this aspect, a longitudinal segment of a peripheral nerve may be enclosed by the reinforced cuff body of the electrode assembly at step 3002. The longitudinal segment of the peripheral nerve may be accessed by any suitable surgical procedure. Any of the peripheral nerves described herein previously are suitable for use with the electrode assembly. The reinforced cuff material may be situated around the exposed longitudinal segment of the peripheral nerve and fastened snugly in place by mechanically engaging the closure elements as described herein previously. The electrodes attached to the inner surface of the cuff body may be situated on preselected regions of the peripheral nerve in an aspect to establish electrical communication with the preselected regions of the peripheral nerve.

In an additional aspect, the protruding end of the lead body may be electrically connected to an electrical device to implement the recording and/or stimulation of the peripheral nerve. Any suitable nerve stimulation device and/or monitoring device known in the art may be electrically connected to the leads of the electrode assembly without limitation. Non-limiting examples of suitable devices include any of the devices described herein previously including, but not limited to, a controller and an electronic data acquisition device. The device may be situated external to the patient in an aspect, and may be implanted within the patient in another aspect.

An electrical stimulus produced by the device may be sent to the electrodes situated within the reinforced cuff body of the electrode assembly at step 3004. The electrical stimulus may be any electrical signal known in the art as an electrical stimulus including, but not limited to one or more fluctuations or waveforms of electrical current or electrical voltage. The amplitude of the electrical signal may be determined by a practitioner of the art based on any one or more of at least several factors including, but not limited to: the size and morphology of the peripheral nerve to be stimulated, the desired intensity of stimulation, the electrical characteristics of the electrode assembly including overall resistance, capacitance, and/or any other relevant electrical characteristic of the electrode assembly, and any combination thereof. In this aspect, the electrical stimulus produced by the device may be sent to the preselected region within the cuff body by way of the one or more leads, which are electrically attached to the electrode at one end and to the device at the opposite end of the lead.

Electrical impulse data may be received by the electrodes situated within the cuff at step 3006. The electrical impulse data may result from earlier stimulation of the peripheral nerve by the electrode assembly, such as may be performed at step 3004 in one aspect. In another aspect, the electrical impulse data may be result from a stimulus applied by another device to another nerve and/or to the same peripheral nerve at a different location. In yet another aspect, the electrical impulse data may be endogenously derived from endogenous firing of the peripheral nerve due to motor commands from the central nervous system or from stimulation of other endogenously firing nerves or from other nerves firing in response to central nervous system commands or other external stimulus including, but not limited to heat, pain, pressure, and any other known external stimulus applied to other tissues and/or organs. Most commonly, the electrical activity of the nerve may be endogenously generated as part of a biological process. In an aspect, the method of using the electrode assembly 3000 may optionally forego the recording of electrical impulse data at step 3006 and instead only send electrical stimuli data at step 3004. In another aspect, the method of using the electrode device 3000 may optionally forego the sending of electrical stimuli at step 3004 and instead only receive electrical impulse data at step 3006.

For example, the electrode assembly may be used to measure and record electrical impulses propagating through a peripheral nerve. At least a portion of the nerve being analyzed may be enclosed with the cuff body of the electrode assembly. As electrical activity is generated in the nerve, the electrical impulses may propagate along the nerve and may be detected by one or more electrodes situated within the cuff body of the electrode assembly.

The electrode assemblies of various aspects described previously herein are suitable for stimulating and recording electrical impulses in small, curved, irregularly shaped, and/or mobile peripheral nerves, cranial nerves, spinal roots, ganglia, or other excitable tissues sensitive to mechanical insult. Similar electrode assemblies may be used for applications involving excitable tissues other than nerves. In another aspect, the electrode assembly may be situated around electrosensitive tissues and/or organs including, but not limited to: ganglia, spinal roots, spinal cord, cardiovascular tissue, muscular tissue, glandular tissue, and any other known electrosensitive tissues or organs that may be stimulated and/or monitored in the treatment of disorders. Non-limiting examples of suitable other applications of the electrode assembly include: the stimulation of muscles such as sphincters in the esophagus, bladder or intestine, thereby stimulating the muscles without mechanically constricting the enclosed structure; functional electrical stimulation of skeletal muscles applied by an external electrode assembly situated around a limb of the body; intravascular stimulation applications using electrode assemblies situated inside and/or contacting the inside wall of blood vessels; other stimulation applications inside or outside of other tubular biological structures.

EXAMPLES

The following examples illustrate various aspects of the electrode assembly and associated reinforced compliant cuff body.

Most, if not all, examples in this section are presented from the standpoint of a flat configuration. That is, although all uses intended for the embodiments exemplified in this section (specifically cuff assemblies) will anticipate a generally cylindrical shape, the discussion and referenced testing will be of examples 'in the flat'. This approach simplifies structural testing and assumes that a change in length of the cuff material 'in the flat' may be construed as equivalent to a change in circumference in a cylinder.

Example 1

Mechanical Properties of Candidate Cuff Body Materials

To assess the mechanical properties of candidate elastic materials for use in the wall of the cuff body, the following experiments were conducted. Force/deflection ratios for a candidate elastomer or elastomer/reinforcement candidate were obtained by subjecting samples of candidate materials to traditional force-deflection testing as described herein below. Samples of the candidate materials were created having a width of 6 mm and a length of 10 mm. The thickness of each sample varied from about 1.2 mm to about 5 mm. Silicone rubber tubing was bonded to each of the 6 mm-long sample edges and a mounting pin was inserted through the tubing at each end to provide a consistent fixture for the application of loads to the sample. During force-deflection testing, the mounting pin at one end was supported at a fixed position and weights were gradually added to the mounting pin at the free end of the sample. The deflection, defined herein as the change in length in the direction of the force induced by the applied weight was recorded along with the amount of weight applied at each step. In this experiment, the weight was applied in a direction that lengthened the sample along the 10 mm dimension of the sample.

Figure 31:
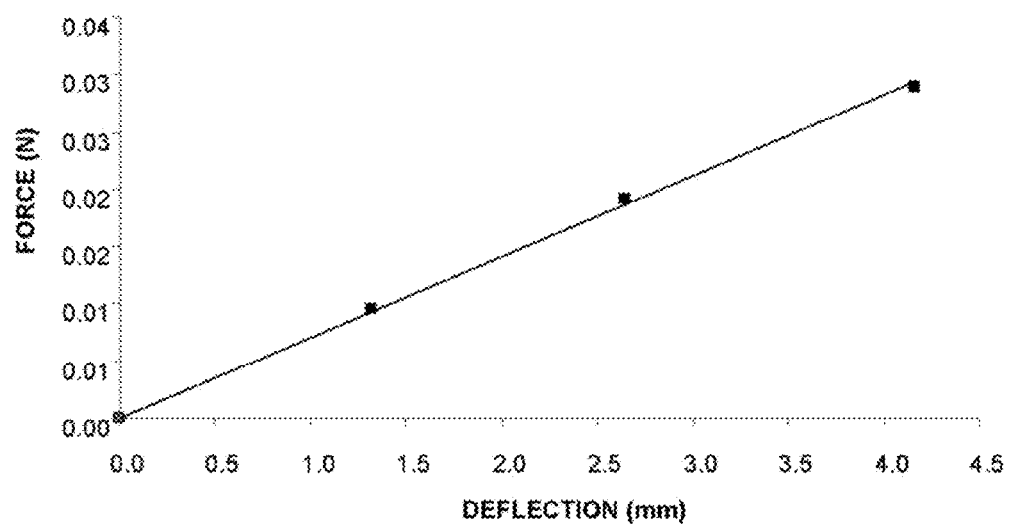
FIG. 31 is a graph summarizing the results of force-deflection testing performed on a prototype elastomer material.
Figure 32:
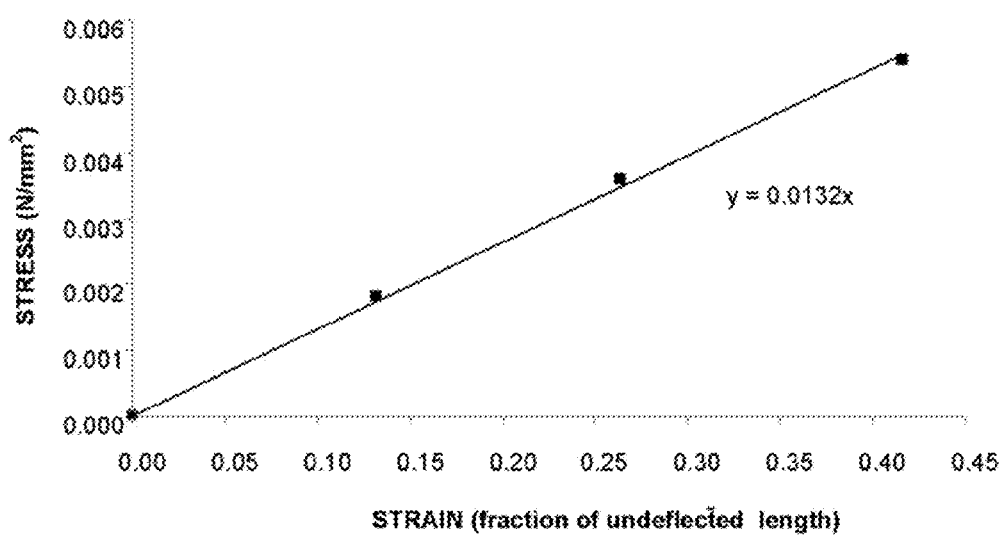
FIG. 32 is a graph summarizing the estimated stress-strain characteristics of a prototype elastomer material
Figure 33:
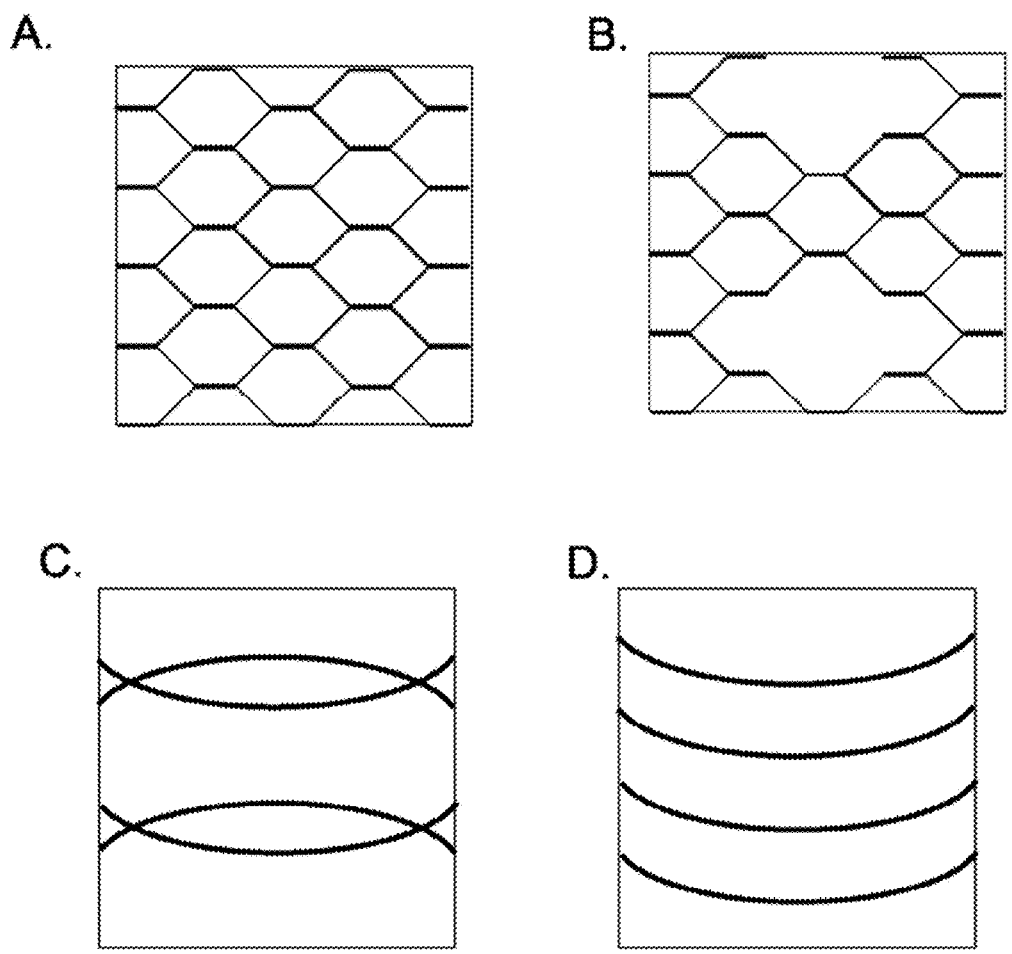
FIGS. 33A-D are top views of candidate cuff body materials subjected to force-deflection testing.

FIG. 31 is a graph summarizing the force-deflection measurements obtained for a sample formed from an isotropic elastomer material. Additional samples were produced using the elastomer along with various reinforcing materials as summarized in Table I. A schematic of four reinforcing materials included in the samples are illustrated in FIGS. 33A-D. The reinforcing materials were either bonded to the external surface of an elastomer layer, sandwiched between two elastomer layers, or embedded within the elastomer layer. The thickness of each sample varied from about 0.250 mm to about 1.8 mm among all the samples tested. The samples were subjected to load-deflection testing as described above and the load/deflection ratio was calculated by obtaining the slope of a linear regression through the measured load-deflection data.

Table I is a summary of the results of the load-deflection analysis, showing the load/deflection ratio estimated for each sample, as well as a summary of the sample's structure and thickness. The load/deflection ratio among the various samples tested varied from about 1.6e-4 N/mm to about 1.3e-3 N/mm. The unreinforced elastomer sample had a load/deflection ratio of 3.5e-4 N/mm and reinforcing the elastomer with any material typically increased the load/deflection ratio by varying degrees.

TABLE I

Material Properties of Reinforced Elastomer Materials

| Sample | Reinforcing Element | Layer Structure | Layer Thickness (mm) | Force/ Deflection (N/mm) |
|---|---|---|---|---|
| 1 | PETKM3003 mesh (see FIG. 33A) | Bonded to elastomer surface | 0.635 | 1.3e−3 |
| 2 | PETKM3003 mesh in clover pattern (see FIG. 33B) | Bonded to elastomer surface | 0.457 | 6.7e−4 |
| 3 | Randomly oriented high modulus PET fibers | Embedded in elastomer layer | 0.254 | 2.8e−4 |
| 4 | PETKM3003 mesh (see FIG. 33A) | Embedded in elastomer layer | 1.140 | 9.8e−4 |
| 5 | PETKM3003 mesh in clover pattern (see FIG. 33B) | Embedded in elastomer layer | 0.508 | 5.12e−4 |
| 6 | PETKM3003 mesh (see FIG. 33A) | Bonded to elastomer surface | 1.020 | 8.7e−4 |
| 7 | Double curved strings (see FIG. 33C) | Embedded in elastomer layer | 0.559 | 3.9e−4 |
| 8 | Randomly oriented high modulus PET fibers | Embedded in elastomer layer | 0.254 | 1.6e−4 |
| 9 | PETKM3003 mesh (see FIG. 33A) | Sandwiched between elastomer layers | 1.778 | 8.7e−4 |
| 10 | None | N/A | 0.686 | 3.5e−4 |
| 11 | Curved threads (see FIG. 33D) | Embedded in elastomer layer | 0.483 | 1.6e−4 |

The results of these experiments determined a range of force/deflection ratios characterizing the structural properties of a variety of reinforced material samples. The force/deflection ratios of the reinforced material samples varied depending on the layer thickness and the type of reinforcing material, as well as how the reinforcing material was incorporated into the elastomer material.

Example 2

Structural Properties of Candidate Prototype Reinforced Cuff Assemblies

To characterize the structural properties of a prototype reinforced cuff body, the following experiments were conducted. Cuff body material samples were constructed with similar dimensions to the samples described in Example 1. In this experiment, a sample was constructed entirely of an elastomer material. The elastomer sample was then subjected to force-deflection testing as described in Example 1.

The sample was then reinforced by bonding a reinforcing layer along the upper and lower edges of the sample, as illustrated in FIG. 12. The reinforcing material was a PETKM3003 mesh material similar to the material illustrated in FIG. 33A. The length of the reinforcing material was 150% of the length of the elastomer material of the sample, allowing the elastomer to stretch to 150% of its original length before structurally engaging the reinforcing material. The reinforced sample was then subjected to similar force-deflection testing as before. Individual fibers within the PETKM3003 mesh material of the reinforced sample were severed in several groups; the reinforced sample with severed individual fibers was subjected to additional force-deflection testing after severing each group of fibers.

Figure 34:
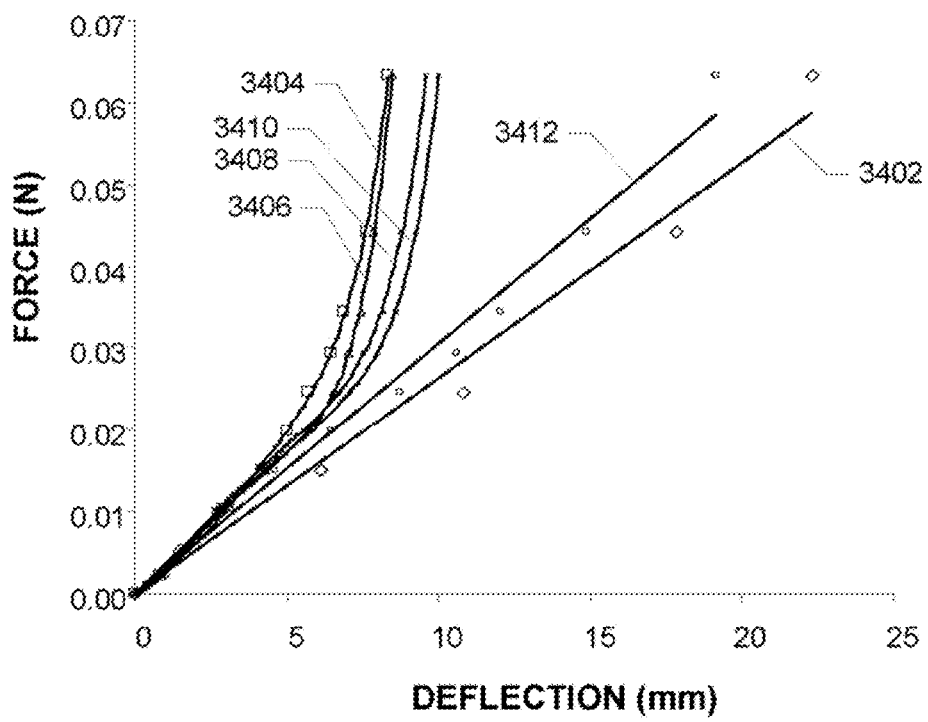
FIG. 34 is a graph summarizing the results of force-deflection testing of a mesh-reinforced cuff body material.

The results of the force-deflection testing are summarized in FIG. 34. The linear regression through the force-deflection data obtained for the unreinforced elastomer material is shown as line 3402. The force-deflection data obtained for the intact reinforced elastomer material is summarized as curve 3404. The force-deflection data for the reinforced elastomer material had a linear trend until the reinforced cuff body stretched about 5 mm, corresponding to a stretched length that was 150% of the original length of the material. Beyond 5 mm of deflection, the slope of the force-deflection data steepened in response to the engagement of the fibers of the reinforcing mesh.

As threads in the reinforcing mesh were selectively cut to attenuate the compliance-reducing effect of the reinforcing material on the sample, the force-deflection curves 3406-3410 were systematically altered. Each of the force-deflection curves 3406-3410 resembled the force deflection curve 3404 for the sample with intact reinforcing material, except that the increase in the slope associated with the engagement of the fibers of the reinforcing material initiated at successively higher deflections. When the reinforcing material was modified to eliminate any continuous strands of reinforcing fibers extending between the ends of the sample, the force-deflection line 3412 was obtained from force-deflection testing. Line 3412 was similar to the data from the unreinforced elastomer material summarized in line 3402.

The results of this experiment confirmed that the structural characteristics of a prototype cuff body may be modified by the addition of a reinforcing material. In particular, reinforcing material added in a mechanically parallel configuration in which the length of the reinforcing material was greater than the length of the elastomer material forming the remainder of the cuff body, would result in a composite cuff body that was compliant within a predetermined range of deflection, with an abrupt reduction in compliance beyond a predetermined threshold deflection.

Example 3

Structural Properties of Candidate Prototype Reinforced Cuff Body with Localized Reinforcement To assess the effects of reinforcement of an elastomer cuff body using an externally-applied reinforcing polymer, the following experiments were conducted. A non-reinforced elastomer sample and a reinforced elastomer material sample were produced and subjected to force-deflection testing using the methods described in Example 1. The reinforcement was applied to the external surface of the elastomer sheet in the form of a silicone polymer coating applied as two diagonally-crossed linear elements as illustrated in FIG. 35A.

Figure 35:
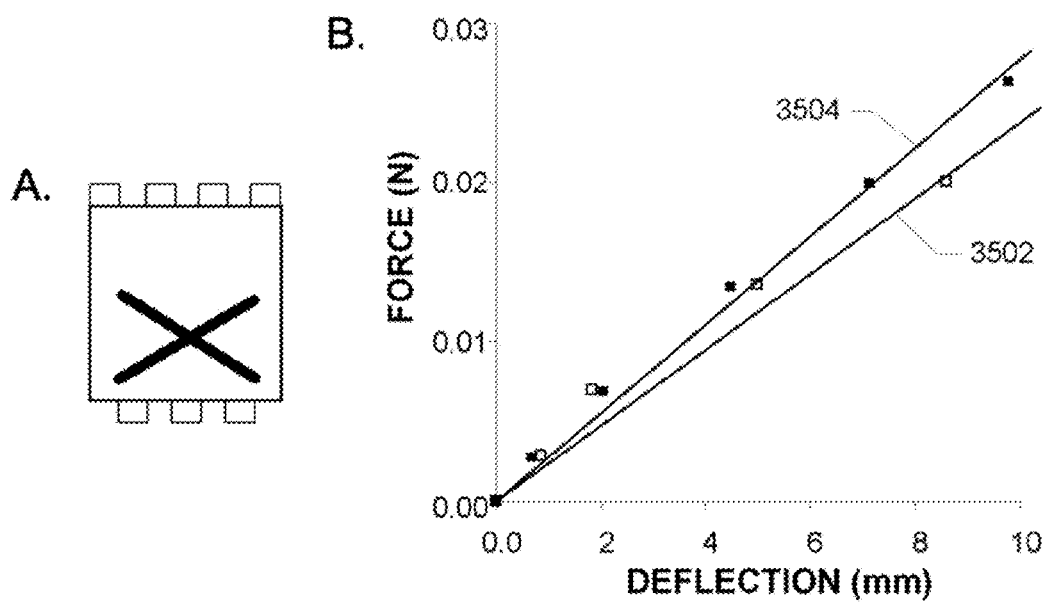
FIG. 35A is a top view of a locally reinforced candidate cuff body material.
FIG. 35B is a graph summarizing the results of force-deflection testing of the locally reinforced candidate cuff body material.

FIG. 35B is a summary of the force-deflection data obtained for the two samples described above. Line 3502 is a regression through the force-deflection data obtained from the unreinforced elastomer sample, and line 3504 is a regression through the force-deflection data obtained from the reinforced material. The addition of the reinforcing polymer altered the force-deflection data for all deflections, rather than just at the larger deflections based on the observations from the reinforced elastomer materials tested in Example 2.

The results of this experiment demonstrated that the force-deflection characteristics were altered at both low and high deflections of the locally reinforced material relative to the unreinforced material. Further, the results of this experiment demonstrated that the force-deflection characteristics of a locally reinforced material may not necessarily be predicted from the force-deflection characteristics of the unreinforced elastomer material. The force-deflection characteristics of a reinforced elastomer material should be verified empirically using, for example, an Instron materials testing device.

Definitions

To facilitate the understanding of the aspects described herein, a number of terms are defined below. Terms defined herein have meanings as commonly understood by a person of ordinary skill in the arts relevant to the aspects described herein. Terms such as "a," "an," and "the" are not intended to refer to only a singular entity, but include the general class of which a specific example may be used for the illustration. The terminology herein is used to describe specific aspects of the present invention, but their usage does not limit the invention to the aspects described herein, except as outlined in the claims.

Compliance, as used herein, refers to a structural property characterized by the degree to which a structure is deformed by an applied force and returns to the structure's original shape after the applied force is removed. A highly compliant structure or a structure with high compliance, as used herein, refers to a structure that readily stretches in response to relatively low applied forces and returns to its original shape after the applied force is removed. A non-compliant structure or a structure with low compliance, as used herein, refers to a structure such as a cuff body that stretches a relatively small amount, if at all, in response to a relatively high applied force. Enhanced or increased compliance, as used herein, refers to a tendency of a structure to stretch more readily under an applied load. Reduced compliance, as used herein, refers to a tendency of a structure to stretch less readily under an applied load. Compliance may be quantified in terms of a force-deflection ratio, defined herein as the force applied to a structure divided by the deflection of the structure in response to the applied force. Deflection, as used herein, refers to a deformation of a structure, such as stretching, compressing, twisting, or bending, typically in response to an applied force.

Mechanical strength, as used herein, refers to a structural property characterized by a resistance to structural damage due to a variety of external loads applied to a structure. For example, a structure having a relatively high mechanical strength is more resistant to structural damage than a structure with relatively low mechanical strength. Non-limiting examples of structural damage include breaking, tearing, irreversible deformation due to stretching, and any other type of structural damage. Mechanical strength and compliance may vary independently between two structures depending on each structure's design. For example, a reinforced structure may possess a similar compliance to an unreinforced structure, but the unreinforced structure may possess a lower mechanical strength. In this example, both the reinforced and unreinforced structures may stretch a similar amount under a similar applied load, but the unreinforced structure may be more vulnerable to structural damage.

A structural property, as used herein, refers to an emergent characteristic of an assemblage of structural elements made up of one or more materials that make up a structure such as an electrode assembly or a cuff body. A structural property, such as compliance or mechanical strength, may be influenced by any number of factors including, but not limited to: the materials contained in the structural elements and associated material properties, the size and dimensions of the structural elements, the environment in which the structure is situated, and the nature of any forces applied to the structure.

A material property, as used herein, refers to an intrinsic property of a material by virtue of the material's composition. A material property, such as elasticity, is independent of the size and dimension of a particular sample of a material or a structural element containing the material.

Elasticity, as used herein, refers to a material property characterized by the degree to which a material is deformed by an applied force and returns to the material's original shape after the applied force is removed. In contrast to compliance, elasticity is independent of the physical size or orientation of the material. The elasticity of a material may be expressed in terms of Young's modulus E, defined as the ratio of the stress of a material divided by the strain of a material. Stress, as used herein, refers to the ratio of an applied force divided by the cross-sectional area of the material through which the force acts. Strain, as used herein, refers to the change in length of a material due to an applied force divided by the material's undeformed length.

Having described the invention in detail, it will be apparent that modifications and variations are possible without departing from the scope of the invention defined in the appended claims. Those of skill in the art should, however, in light of the present disclosure, appreciate that many changes could be made in the specific embodiments that are disclosed and still obtain a like or similar result without departing from the spirit and scope of the invention, therefore all matter set forth herein is to be interpreted as illustrative and not in a limiting sense.

What is claimed is:

1. A reinforced compliant cuff body comprising:
   a compliant cuff body bounded by opposed and parallel first and second longitudinal edges, wherein the compliant cuff body further comprises opposed inner and outer surfaces; and
   one or more reinforcing elements attached to the compliant cuff body;
   wherein:
      the mechanical strength of the reinforced compliant cuff body is greater than the mechanical strength of the compliant cuff body alone;
      the first and second longitudinal edges are joined to form the reinforced compliant cuff body into a tubular shape enclosing a lumen bounded by the inner surface, wherein a nerve is situated within the lumen; and
      the reinforced compliant cuff body stretches to accommodate a deflection of the nerve within a safe compliance region.

2. The reinforced compliant cuff body of claim 1, wherein the compliant cuff body is formed from an elastomer chosen from: a silicone rubber, a silicone adhesive dispersion, a urethane rubber, a urethane adhesive dispersion, and any combination thereof.

3. The reinforced compliant cuff body of claim 1, wherein the compliant cuff body further comprises a thickness extending between the inner surface and the outer surface ranging from about 0.010 mm to about 1 mm.

4. The reinforced compliant cuff body of claim 1, wherein the one or more reinforcing elements is attached to the outer surface of the compliant cuff body.

5. The reinforced compliant cuff body of claim 1, wherein the one or more reinforcing elements is attached to the inner surface of the compliant cuff body.

6. The reinforced compliant cuff body of claim 1, wherein the one or more reinforcing elements is embedded within the compliant cuff body between the outer surface and the inner surface of the compliant cuff body.

7. The reinforced compliant cuff body of claim 1, wherein a circumferential compliance of the reinforced compliant cuff body in a circumferential direction is essentially the same as the circumferential compliance of the compliant cuff body in the circumferential direction, wherein the circumferential direction is mutually perpendicular to the first and second longitudinal edges.

8. The reinforced compliant cuff body of claim 1, wherein the one or more reinforcing elements are selected from: a reinforcing polymer, a reinforcing textile, and any combination thereof.

9. The reinforced compliant cuff body of claim 8, wherein the one or more reinforcing elements are selected from a reinforcing particle, a reinforcing strand, a reinforcing sheet, a reinforcing coating, a reinforcing fiber, a reinforcing fabric, a reinforcing mesh, and any combination thereof.

10. The reinforced compliant cuff body of claim 9, wherein the one or more reinforcing elements consist of a reinforcing mesh defining a plurality of openings, wherein the reinforcing mesh is embedded within the compliant cuff body between the outer surface and the inner surface of the compliant cuff body and wherein a mesh area of the reinforcing mesh is essentially equal to a sheet area of the compliant cuff body.

11. The reinforced compliant cuff body of claim 8, wherein the one or more reinforcing elements are attached at a first attachment situated on the outer surface of the compliant cuff body at the first longitudinal edge and at a second attachment situated on the outer surface of the compliant cuff body at the second longitudinal edge.

12. The reinforced compliant cuff body of claim 11, wherein each of the one or more reinforcing elements comprises a reinforcing length extending between the first attachment and the second attachment, wherein the reinforcing length is longer than the distance between the first and second longitudinal edges of the compliant cuff body.

13. The reinforced compliant cuff body of claim 12, wherein the reinforcing length is about 150% of the distance between the first and second longitudinal edges of the compliant cuff body.

14. The reinforced compliant cuff body of claim 9, wherein the reinforcing polymer is embedded within the compliant cuff body between the outer surface and the inner surface of the compliant cuff body, attached to the inner surface or the outer surface of the compliant cuff body, painted on to the inner surface or the outer surface of the compliant cuff body, or attached within one or more depressions formed within the inner surface or the outer surface of the compliant cuff body.

15. The reinforced compliant cuff body of claim 14, wherein the reinforcing polymer is an electrically conductive polymer.

16. The reinforced compliant cuff body of claim 15, wherein the electrically conductive polymer is exposed on the inner surface and forms an electrode.

17. The reinforced compliant cuff body of claim 15, wherein the electrically conductive polymer is insulated using a non-conductive polymer and forms a lead.

18. The reinforced compliant cuff body of claim 1, wherein the safe compliance region comprises a range of stretching of the reinforced compliant cuff body characterized by accommodation of a change in nerve diameter to about 150% of an original nerve diameter while exerting a reactive force over the inner surface that is less than or equal to a nerve damage threshold pressure.

19. A reinforced compliant cuff body comprising:
a compliant reinforcing mesh bounded by opposed parallel first and second longitudinal edges, the mesh comprising a network of interconnected fibers defining a plurality of openings; and
a compliant coating attached to the reinforcing mesh, wherein the compliant coating surrounds each of the interconnected fibers and forms a film spanning each of the plurality of openings.

20. The reinforced compliant cuff body of claim 19, wherein a longitudinal compliance of the reinforced compliant cuff body in a longitudinal direction parallel to the first and second longitudinal edges is less than a circumferential compliance in a circumferential direction mutually perpendicular to the first and second longitudinal edges.

21. The reinforced compliant cuff body of claim 19, wherein the first and second longitudinal edges are joined to form the cuff body into a tubular shape enclosing a lumen with an unstretched lumen diameter.

22. The reinforced compliant cuff body of claim 21, wherein the cuff body stretches in response to a lumen pressure and encloses an increased lumen diameter, wherein the increased lumen diameter is at least 150% of the unstretched lumen diameter when the lumen pressure is about 20 mm Hg.

23. The reinforced compliant cuff body of claim 19, wherein the compliant coating is formed from an elastomer chosen from: a silicone rubber, a silicone adhesive dispersion, a urethane rubber, a urethane adhesive dispersion, and any combination thereof.

24. The reinforced compliant cuff body of claim 19, wherein the film spanning each of the plurality of openings as a thickness of less than about 0.125 mm.

25. The reinforced compliant cuff body of claim 24, wherein the film spanning each of the plurality of openings has a thickness ranging from about 0.050 mm to about 0.075 mm.

26. An electrode assembly comprising:
a compliant cuff body bounded by opposed parallel first and second longitudinal edges and comprising opposed inner and outer surfaces;
one or more reinforcing elements attached to the compliant cuff body;
at least one electrode attached to the inner surface of the compliant cuff body; and
at least one lead comprising an elongate conductive element electrically connected to the at least one electrode at an attached end;
wherein:
the at least one lead extends from the electrode to the outer surface of the compliant cuff body;
the mechanical strength of the electrode assembly is greater than the mechanical strength of the compliant cuff body alone;
the first and second longitudinal edges are joined to form the electrode assembly into a tubular shape enclosing a lumen bounded by the inner surface, wherein a nerve is situated within the lumen; and
the electrode assembly stretches to accommodate a deflection of the nerve within a safe compliance region.

27. The electrode assembly of claim 26, wherein a longitudinal compliance of the electrode assembly is reduced in a longitudinal direction essentially parallel to the first and second longitudinal edges of the compliant cuff body.

28. The electrode assembly of claim 26, wherein at least a portion of the one or more reinforcing elements is situated at or near the at least one electrode.

29. The electrode assembly of claim 26, further comprising a lead body, wherein the lead body comprises:
a body attached end attached to the outer surface of the compliant cuff body at a region within which at least one lead projects from the outer surface; and a body free end opposite to the body attached end projecting from the outer surface of the compliant cuff body;

wherein each segment of the at least one lead projecting from the outer surface is contained within the lead body.

30. The electrode assembly of claim 29, wherein at least a portion of the one or more reinforcing elements are situated at or near the body attached end.

31. The electrode assembly of claim 30, wherein at least a portion of the one or more reinforcing elements extend into the lead body at the body attached end.

32. The electrode assembly of claim 26, wherein at least a portion of the at least one lead including the attached end comprises a compliant conductor electrically attached to an electrode on the inner surface of the compliant cuff body.

33. The electrode assembly of claim 26, wherein the safe compliance region comprises a range of stretching of the electrode assembly characterized by accommodation of a change in nerve diameter to about 150% of an original nerve diameter while exerting a reactive force over the inner surface that is less than or equal to a nerve damage threshold pressure.

34. The electrode assembly of claim 33, wherein the compliant cuff body forms a continuous layer of electrical insulation around the lumen.

35. The electrode assembly of claim 34, wherein a nerve is situated within the lumen and the at least one electrode is maintained in close proximity to the nerve before, during, and after changes in nerve size or shape.

36. A method of producing a reinforced cuff body comprising:

contacting a reinforcing mesh comprising a network of interconnected fibers defining a plurality of openings with an uncured liquid elastic material to coat the fibers and to form a film across the plurality of openings; and curing the uncured liquid elastic material to form an elastic material coating over the reinforcing mesh and the plurality of openings.

37. The method of claim 36, wherein the uncured liquid elastic material is chosen from: uncured silicone rubber, uncured silicone adhesive dispersion, uncured urethane rubber, uncured urethane adhesive dispersion, and any combination thereof.

38. The method of claim 36, wherein the film across each of the plurality of openings has a thickness of less than about 0.125 mm.

39. The method of claim 36, wherein the film across each of the plurality of openings has a thickness ranging from about 0.050 mm to about 0.075 mm.

40. The method of claim 36, further comprising:

trimming the reinforcing mesh to a desired size bounded by opposed and parallel first and second longitudinal edges;

affixing a plurality of closure elements along the first and second longitudinal edges; and joining the first and second longitudinal edges to form a generally tubular shape with the reinforcing mesh.

41. The reinforced compliant cuff body of claim 18, wherein the wherein the nerve damage threshold pressure is about 20 mm Hg.

42. The electrode assembly of claim 33, wherein the nerve damage threshold pressure is about 20 mm Hg.

* * * * *